United States Patent
Koch et al.

(10) Patent No.: US 11,871,691 B2
(45) Date of Patent: Jan. 16, 2024

(54) AGRICULTURAL IMPLEMENTS FOR SOIL AND VEGETATION ANALYSIS

(71) Applicant: Climate LLC, Saint Louis, MO (US)

(72) Inventors: Dale Koch, Tremont, IL (US); Todd Swanson, Morton, IL (US); Kent Levy, Morton, IL (US); Adam Vaccari, Peoria, IL (US); Jason Stoller, Eureka, IL (US)

(73) Assignee: CLIMATE LLC, Saint Louis, MO (US)

( * ) Notice: Subject to any disclaimer, the term of this patent is extended or adjusted under 35 U.S.C. 154(b) by 0 days.

(21) Appl. No.: 16/922,506

(22) Filed: Jul. 7, 2020

(65) Prior Publication Data

US 2020/0396893 A1    Dec. 24, 2020

Related U.S. Application Data

(62) Division of application No. 15/806,014, filed on Nov. 7, 2017, now Pat. No. 10,701,856.
(Continued)

(51) Int. Cl.
*A01B 79/00* (2006.01)
*A01D 41/127* (2006.01)
(Continued)

(52) U.S. Cl.
CPC ............ *A01B 79/005* (2013.01); *A01B 79/02* (2013.01); *A01C 21/007* (2013.01);
(Continued)

(58) Field of Classification Search
CPC ............ G01N 1/20; G01N 1/286; G01N 1/10;
G01N 1/12; G01N 1/16; G01N 1/2273;
G01N 1/08; G01N 1/125; G01N
2001/1043; G01N 1/04; G01N 33/362;
G01N 1/28; G01N 2001/021; G01N
2001/085; G01N 2001/4061; G01N
2033/245; G01N 33/24; E21B 49/025;
E21B 49/02; E21B 25/00; E21B 7/046;
E21B 19/08; E21B 7/021;
(Continued)

(56) References Cited

U.S. PATENT DOCUMENTS 3,091,969 A    6/1963   Romanchuk
3,224,512 A   12/1965   Alexander
(Continued)

FOREIGN PATENT DOCUMENTS

BR    PI0800802 A2    11/2009
BR    PI1106191 A2     8/2013
(Continued)

OTHER PUBLICATIONS

European Patent Office, "Search Report" in application No. 17867783.7-1004, dated Jun. 26, 2020, 12 pages.
(Continued)

*Primary Examiner* — John Fitzgerald
*Assistant Examiner* — Truong D Phan
(74) *Attorney, Agent, or Firm* — Harness, Dickey & Pierce, P.L.C.

(57) ABSTRACT

Described herein are implements that include a vehicle having a system for sensing or testing soil and/or vegetation as the vehicle traverses a field.

16 Claims, 43 Drawing Sheets

Related U.S. Application Data

(60) Provisional application No. 62/418,650, filed on Nov. 7, 2016.

(51) Int. Cl.
| | |
|---|---|
| *A01C 21/00* | (2006.01) |
| *A01B 79/02* | (2006.01) |
| *G01N 1/08* | (2006.01) |
| *G01N 1/28* | (2006.01) |
| *G01N 33/24* | (2006.01) |
| *G01N 1/40* | (2006.01) |
| *G01N 1/02* | (2006.01) |

(52) U.S. Cl.
CPC ............ *A01D 41/127* (2013.01); *G01N 1/08* (2013.01); *G01N 1/28* (2013.01); *G01N 33/24* (2013.01); *G01N 2001/021* (2013.01); *G01N 2001/085* (2013.01); *G01N 2001/4061* (2013.01); *G01N 2033/245* (2013.01)

(58) Field of Classification Search
CPC .. E21B 7/02; E21B 7/26; B23Q 5/265; B23Q 5/326; B23Q 16/003; E01C 23/124; E04H 17/263; A01B 79/005; A01B 79/02; A01C 21/007; A01D 41/127
See application file for complete search history.

(56) References Cited

U.S. PATENT DOCUMENTS

| | | | |
|---|---|---|---|
| 3,618,447 A | 11/1971 | Goins | |
| 3,752,651 A | 8/1973 | Bush | |
| 4,174,178 A * | 11/1979 | Ouchi | G01N 27/44704 118/225 |
| 4,252,200 A | 2/1981 | Peterson | |
| 4,327,661 A | 5/1982 | Boeckel | |
| 4,383,583 A | 5/1983 | Baker | |
| 5,033,397 A * | 7/1991 | Colburn, Jr. | A01M 7/0089 111/118 |
| 5,121,643 A | 6/1992 | Voloudakis | |
| 5,246,862 A | 9/1993 | Grey et al. | |
| 5,337,620 A | 8/1994 | Kalidini | |
| 5,355,815 A | 10/1994 | Monson | |
| 5,394,949 A | 3/1995 | Wright | |
| 5,408,893 A | 4/1995 | McLeroy | |
| 5,411,103 A | 5/1995 | Werner | |
| 5,461,229 A | 10/1995 | Sauter et al. | |
| 5,526,705 A | 6/1996 | Skotnikov et al. | |
| 5,528,543 A | 6/1996 | Stiegler | |
| 5,673,637 A | 10/1997 | Colburn, Jr. et al. | |
| 5,741,983 A | 4/1998 | Skotnikov | |
| 6,016,713 A * | 1/2000 | Hale | A01B 79/005 73/864.45 |
| 6,041,582 A | 3/2000 | Tiede et al. | |
| 6,070,673 A | 6/2000 | Wendte | |
| 6,094,999 A | 8/2000 | DuBois | |
| 6,138,590 A | 10/2000 | Colburn, Jr. | |
| 6,176,326 B1 | 1/2001 | David | |
| 6,242,261 B1 | 6/2001 | Schoenau et al. | |
| 6,327,569 B1 | 12/2001 | Reep | |
| 6,339,966 B1 | 1/2002 | Kalidindi | |
| 6,363,803 B1 | 4/2002 | Hubers | |
| 6,391,262 B1 | 5/2002 | Brinton et al. | |
| 6,393,926 B1 | 5/2002 | Bowersox | |
| 6,484,652 B1 | 11/2002 | Colburn et al. | |
| 6,549,851 B2 | 4/2003 | Greensides | |
| 6,608,672 B1 | 8/2003 | Shibusawa et al. | |
| 6,766,865 B1 * | 7/2004 | Dagel | G01N 33/24 172/457 |
| 6,937,939 B1 | 8/2005 | Shibusawa et al. | |
| 7,047,135 B2 | 5/2006 | Dyer et al. | |
| 7,216,555 B2 | 5/2007 | Drummond et al. | |
| 7,255,016 B2 | 8/2007 | Burton | |
| 7,299,686 B2 | 11/2007 | Briaud et al. | |
| 7,507,583 B2 | 3/2009 | Maxwell, III | |
| 7,662,217 B2 | 2/2010 | O'Brien et al. | |
| 7,692,789 B1 | 4/2010 | Ebinger et al. | |
| 7,827,873 B2 | 11/2010 | Burton | |
| 7,927,883 B2 | 4/2011 | Tuli et al. | |
| 7,966,165 B2 | 6/2011 | Asaoka et al. | |
| 8,573,074 B1 | 11/2013 | Marker | |
| 8,613,234 B1 | 12/2013 | Harrell | |
| 8,656,760 B2 | 2/2014 | Johnson et al. | |
| 8,734,734 B2 | 5/2014 | Kido et al. | |
| 8,744,772 B1 | 6/2014 | Magro et al. | |
| 8,849,523 B1 | 9/2014 | Chan | |
| 8,955,401 B1 | 2/2015 | Burton | |
| 9,116,078 B1 | 8/2015 | Scheiderer et al. | |
| 9,485,985 B2 | 11/2016 | Hyde | |
| 10,073,074 B1 | 9/2018 | Kumar et al. | |
| 10,102,473 B1 | 10/2018 | Anderson et al. | |
| 10,393,722 B2 | 8/2019 | Koshnick | |
| 10,564,122 B1 | 2/2020 | Xu et al. | |
| 2001/0053336 A1 | 12/2001 | Hammer et al. | |
| 2002/0102186 A1 * | 8/2002 | McEntee | B65D 75/327 422/552 |
| 2003/0112152 A1 | 6/2003 | Pickett | |
| 2004/0095154 A1 | 5/2004 | Lundstrom et al. | |
| 2005/0172733 A1 | 8/2005 | Drummond et al. | |
| 2006/0121620 A1 * | 6/2006 | Bhandari | G01N 31/227 436/110 |
| 2006/0254371 A1 | 11/2006 | Shiloni et al. | |
| 2007/0125508 A1 | 6/2007 | McVane | |
| 2007/0272004 A1 | 11/2007 | Rode et al. | |
| 2008/0083263 A1 | 4/2008 | Philipp et al. | |
| 2008/0096044 A1 * | 4/2008 | Matsumoto | C25D 3/38 428/623 |
| 2008/0195268 A1 | 8/2008 | Sapilewski | |
| 2008/0298166 A1 | 12/2008 | Cartagena | |
| 2009/0071714 A1 | 3/2009 | Shrestha | |
| 2009/0181451 A1 | 7/2009 | Slowey et al. | |
| 2010/0037712 A1 | 2/2010 | Burton | |
| 2010/0283993 A1 | 11/2010 | Preiner et al. | |
| 2010/0291619 A1 | 11/2010 | Ronnie et al. | |
| 2011/0240730 A1 | 10/2011 | Covely | |
| 2011/0299085 A1 | 12/2011 | Preiner et al. | |
| 2012/0000298 A1 | 1/2012 | Cox | |
| 2012/0002192 A1 | 1/2012 | Preiner et al. | |
| 2012/0103077 A1 | 5/2012 | Koshnick et al. | |
| 2012/0128549 A1 | 5/2012 | Zhou et al. | |
| 2012/0222500 A1 | 9/2012 | Riess et al. | |
| 2012/0308306 A1 | 12/2012 | Kruse | |
| 2012/0315635 A1 | 12/2012 | Vangbo et al. | |
| 2013/0139474 A1 | 6/2013 | Coleman | |
| 2013/0283925 A1 | 10/2013 | White et al. | |
| 2013/0319763 A1 | 12/2013 | McGraw | |
| 2014/0012504 A1 | 1/2014 | Ben-Dor et al. | |
| 2014/0048001 A1 | 2/2014 | Bassett | |
| 2014/0069184 A1 | 3/2014 | McAlary et al. | |
| 2014/0097198 A1 | 4/2014 | Lazaris et al. | |
| 2014/0234949 A1 * | 8/2014 | Wasson | G01N 35/00871 435/287.2 |
| 2014/0251032 A1 | 9/2014 | Scheiderer et al. | |
| 2014/0273253 A1 | 9/2014 | Roberts et al. | |
| 2014/0329330 A1 | 11/2014 | Williams et al. | |
| 2014/0345394 A1 | 11/2014 | Schildroth | |
| 2014/0358381 A1 | 12/2014 | Holland | |
| 2014/0365084 A1 | 12/2014 | Chan et al. | |
| 2014/0379228 A1 | 12/2014 | Batcheller et al. | |
| 2015/0076567 A1 | 3/2015 | Stimpson et al. | |
| 2015/0087072 A1 | 3/2015 | Adamchuck et al. | |
| 2015/0088785 A1 | 3/2015 | Chi | |
| 2015/0305226 A1 | 10/2015 | Zemenchik | |
| 2015/0305227 A1 | 10/2015 | Zemenchik et al. | |
| 2015/0305228 A1 | 10/2015 | Zemenchik | |
| 2015/0323491 A1 | 11/2015 | Miller et al. | |
| 2015/0373905 A1 * | 12/2015 | Anderson | A01C 21/00 701/50 |
| 2015/0377853 A1 | 12/2015 | Feng et al. | |
| 2016/0018380 A1 | 1/2016 | Gerber-Siff et al. | |
| 2016/0023204 A1 | 1/2016 | Scaff et al. | |
| 2016/0116632 A1 | 4/2016 | Stoller et al. | |
| 2016/0123952 A1 | 5/2016 | Huluka | |

(56) References Cited

U.S. PATENT DOCUMENTS

| | | |
|---|---|---|
| 2016/0169855 A1 | 6/2016 | Baity |
| 2016/0223511 A1 | 8/2016 | Koshnick et al. |
| 2016/0274009 A1 | 9/2016 | White et al. |
| 2016/0349167 A1 | 12/2016 | Eising |
| 2017/0045488 A1 | 2/2017 | Riess et al. |
| 2017/0045489 A1 | 2/2017 | Sauder et al. |
| 2017/0067843 A1 | 3/2017 | Rouchon et al. |
| 2017/0108441 A1 | 4/2017 | Nault et al. |
| 2017/0191905 A1* | 7/2017 | Giles ................. G01N 1/08 |
| 2017/0223947 A1 | 8/2017 | Gall et al. |
| 2017/0231151 A1 | 8/2017 | Cartwright |
| 2017/0241973 A1 | 8/2017 | Chan et al. |
| 2017/0261986 A1 | 9/2017 | Gerrish |
| 2017/0286574 A1 | 10/2017 | Chappell |
| 2017/0295715 A1 | 10/2017 | Gerrish |
| 2017/0299511 A1 | 10/2017 | Palassis et al. |
| 2017/0311559 A1 | 11/2017 | Ebert et al. |
| 2017/0322142 A1 | 11/2017 | Handique et al. |
| 2017/0366877 A1 | 12/2017 | Basheer et al. |
| 2018/0010987 A1 | 1/2018 | Lynk |
| 2018/0020611 A1 | 1/2018 | LaRowe |
| 2018/0080914 A1 | 3/2018 | Baucom |
| 2018/0124992 A1 | 5/2018 | Koch |
| 2018/0156697 A1 | 6/2018 | Fiechter |
| 2018/0172659 A1 | 6/2018 | Visser |
| 2018/0185845 A1 | 7/2018 | Bridle et al. |
| 2018/0188225 A1 | 7/2018 | Viscarra Rossel et al. |
| 2018/0259674 A1 | 9/2018 | Hu et al. |
| 2018/0310456 A1 | 11/2018 | Zemenchik et al. |
| 2018/0322590 A1 | 11/2018 | Sundararajan et al. |
| 2018/0333894 A1 | 11/2018 | Story et al. |
| 2018/0356389 A1 | 12/2018 | Willness |
| 2018/0364157 A1 | 12/2018 | Ghiraldi et al. |
| 2019/0017984 A1 | 1/2019 | Fang |
| 2019/0101505 A1 | 4/2019 | Liu et al. |
| 2019/0107467 A1 | 4/2019 | Case |
| 2019/0285608 A1 | 9/2019 | Laird et al. |
| 2020/0128720 A1 | 4/2020 | Cizek et al. |
| 2020/0128721 A1 | 4/2020 | Lewis et al. |
| 2020/0184214 A1 | 6/2020 | Casas et al. |

FOREIGN PATENT DOCUMENTS

| | | |
|---|---|---|
| CN | 104198445 A | 12/2014 |
| CN | 104483285 A | 4/2015 |
| DE | 202015000747 U1 | 4/2015 |
| DE | 202017107128 U1 | 12/2017 |
| DE | 102017127763 A1 | 5/2019 |
| EP | 0157082 A2 * | 10/1985 |
| EP | 2455739 A1 | 5/2015 |
| EP | 2868806 B1 | 5/2015 |
| EP | 3200958 A1 | 8/2017 |
| EP | 3379247 A1 | 9/2018 |
| EP | 3450986 A1 | 3/2019 |
| FR | 3043778 | 5/2017 |
| JP | 3451535 | 3/1999 |
| WO | WO98/53312 | 11/1998 |
| WO | WO2012/122050 A2 | 9/2012 |
| WO | WO2016/025848 A1 | 2/2016 |
| WO | WO2016/193898 A1 | 12/2016 |
| WO | WO2017085415 A1 | 5/2017 |
| WO | WO2017096418 A1 | 6/2017 |
| WO | WO2017/155411 A1 | 9/2017 |
| WO | WO2018101843 | 1/2018 |
| WO | WO2018094497 A1 | 5/2018 |
| WO | WO2018182393 A1 | 10/2018 |
| WO | WO2019028540 A1 | 2/2019 |
| WO | WO2019166992 A2 | 9/2019 |
| WO | WO2019072729 A1 | 4/2020 |

OTHER PUBLICATIONS

European Claims in application No. 17867783.7-1004, dated Jun. 2020, 4 pages.
Australian Patent Office, "Search Report" in application No. 2017355728 dated Jul. 30, 2020, 6 pages.
Australian Claims in application No. 2017355728, dated Jul. 2020, 4 pages.
Argentina Patent Office, "Search Report" in application No. P170103090, dated Nov. 11, 2020, 4 pages.
Argentina Claims in application No. P170103090, dated Nov. 2020, 5 pages.
Canda Patent Office, "Office Action" in application No. 3,043,170, dated Feb. 18, 2021, 4 pages.
Canada Claims in application No. 3,043,170, dated Feb. 18, 2021, 4 pages.
Brazil Patent Office, "Written Opinion" in application No. BR1120190093087, dated Jan. 8, 2021, 15 pages.
Brazil Patent Office, "Office Action" in application No. BR122020022711-7, dated Apr. 16, 2021, 13 pages.
Brazil Patent Office, "Office Action and Written Opinion" in application No. BR122020022711-7 , dated Jan. 11, 2021, 26 pages.
Brazil Claims in application No. BR122020022711-7, dated Jan. 11, 2021, 6 pages.
Brazil Claims in application No. BR122020022711-7, dated Apr. 16, 2021, 5 pages.
Brazil Claims in application No. BR1120190093087, dated Jan. 8, 2021, 2 pages.
Alves Franca et al., "Chapter 31 Tests for Color in Lovibond and ASTM Colorimeters", Minerals Treatment Laboratory Practices, dated 2007, 47 pages.
Koch, U.S. Appl. No. 15/806,014, filed Nov. 7, 2017, Restriction Requirement, dated Dec. 19, 2019.
Koch, U.S. Appl. No. 15/806,014, filed Nov. 7, 2017, Notice of Allowance, dated May 21, 2020.
Koch, U.S. Appl. No. 15/806,014, filed Nov. 7, 2017, Office Action, dated Feb. 27, 2020.
Koch, U.S. Appl. No. 15/806,014, filed Nov. 7, 2017, Interview Summary, dated Apr. 17, 2020.
Koch, U.S. Appl. No. 15/806,014, filed Nov. 7, 2017, Final Office Action, dated Apr. 24, 2020.
Geoprospectors, "Topsoil Mapper", Functional Layout, dated 2016, 2 pages.
A & L Eastern Laboratories, "How to Take a Plant Sample for Plant Analysis", http://www.aleastern.com/taking_plant_sample.aspx, last viewed on Sep. 9, 2016, 4 pages.
Kim et al., "Simultaneous Analysis of Soil Macronutrients Using Ion-Selective Electrodes", SSSAJ: vol. 71, No. 6, Dated Nov.-Dec. 2007, 11 pages.
Horiba Labs, "Soil Nitrate Measurement for Determination of Plant-Available Nitrogen", dated Feb. 2015, 2 pages.
Horiba Labs, "Measurement of Potassium in Soil", LAQUA Twin, Application Note, dated 2013 2 pages.
Horiba labs, "Compact Water Quality Meter", Laquatwin, http://www.horiba.com/laquatwin/en/lineup/index.html, last viewed on Aug. 18, 2016, 2 pages.
He et al., "Prediction of Soil Content Using Near-infrared Spectroscopy", SPIE Newsroom, dated 2006, 3 pages.
Hanson, Roger, "Sampling Plant Tissue and Soil", University of Missouri Extension, dated Oct. 1993, 3 pages.
Mallarino, Antonio, Soil Phosphorus Tests in the North-Central Region, Powerpoint, Lowa State University, dated Mar. 14, 2005, 36 pages.
Geoprospectors, "Topsoil Mapper", Soil Information, dated 2016, 2 pages.
Meeting Oct. 14, 2015 (JJH, DMK, TS, JJS, TLP), 1 page.
Force A, "Multiplex 330", http://www.force-a.com/en/capteurs-scientifiques/multiplex-330/, last viewed on Sep. 2, 2016, 7 pages.
Force A, "Dualex Scientific", http://www.force-a.com/en/capteurs-scientifiques/dualex-scientific/, last viewed on Sep. 2, 2016, 8 pages.
Feng et al., "Detection of Soil Total Nitrogen by Vis-SWNIR Spectroscopy", CCTA dated 2010, Part IV, IFIP AICT 347, 8 pages.
Department of Sustainable Natural Resources, "Soil Survey Standard Test Method Available Phosphorus: Bray No. 1 Extract", dated 1995, 4 pages.

(56) References Cited

OTHER PUBLICATIONS

Current Claims in application no. PCT/US2017/060460, dated Feb. 2019, 4 pages.
Cornell University Cooperative Extension, "Phosphorus Soil Testing Methods", Agronomy Fact Sheet Series, Fact Sheet 15, dated 2010, 2 pages.
Ciesla et al., "Use of Ion-selective Electrodes for Determination of Content of Potassium in Egner-Rhiem Soil Extracts", RES. AGR. ENG., 53, dated 2007 (1), 5 pages.
Adsett et al., "In-Field Measurement of Soil Nitrate Using an Ion-Seective Electrode", www.intechopen.com, dated Apr. 1, 2010, 29 pages.
Geoprospectors, "Topsoil Mapper", System Components, dated 2016, 2 pages.
Spectrum Analytic Inc., "Illustrated Guide to Sampling for Plant Analysis", dated 2009, 8 pages.
www.metos.at, "Metos NPK, Measure Your Fertilizer Requirements and Save Money and the Environment", dated 2014, 2 pages.
Wojciechowski et al., "Proceedings of the Institute of Vehicles", dated 2013, 10 pages.
Watson, "Understanding Soil Tests for Plant-Available Phosphorus", the Ohio State University Extension, dated 2007, 4 pages.
Volpe et al., "The Rocky 7 Mars Rover Prototype", Published in the proceedings of IEEE-RSJ International Conference on Intelligent Robots and Systems, dated Nov. 4-8, 1996 Osaka Japan, 7 pages.
Vittorio, "Model 250 Food Strainer", http;//www.victorio.info/food-strainer.html, dated 2016, 2 pages.
Tiruneh, Getachew, "Rapid Soil Quality Assessment Using Portable Visible Near Infrared (VNIR) Spectroscopy", dated 2014, 47 pages.
Thom et al., "Sampling for Corn Plant Tissue Analysis", National Corn Handbook, Crop Fertilization, Iowa State University, dated Sep. 1991, 2 pages.
Maleki et al., "On-the-go Variable-Rate Phosphprus Fertilisation Based on a Visible and Near-infrared Soil Senser", dated Sep. 13, 2007, 12 pages.
Stenberg et al., "Visible and Near Infrared Spectroscopy in Soil Science", Advances in Agronomy, vol. 107, Academic Press dated 2010, 44 pages.
Zhang et al., "Mehlich 3 Extraction for Macro- and Micronutrients", dated 2011, 5 pages.
Soil Doctors System Provides, "Combine Soil Mapping and Synchronized Yield Analysis" dated Nov. 26, 2001, http://www.colburn.bluedomino.com/CMapPR.htm, 7 pages.
Sinfiled et al., "Evaluation of Sensing Technologies for On-the-Go Detection of Macro-nutrients in Cultivated Soils", Computers and Electronics in Agriculture, dated Sep. 2009, 18 pages.
Shaw, "Assessing the Potential for Ion Selective Electrodes and Dual Wavelength UV Spectroscopy as a Rapid on-Farm Measurement of Soil Nitrate Concentration", dated Jul. 2, 2013, 15 pages.
Ruen, Jim, "Sensors Drive Greater Data Value", dated Oct. 13, 2016, 4 pages.
Pessl Instruments, "The Lab-on-a-Chip System Metos NPK", Redagricola, Chile dated Jun. 3, 2015, 28 pages.
Penn State Extension, "Plant Tissue Analysis", the Agronomy Guide, http://extension.psu.edu/agronomy-guide/cm/sec2/sec26, last viewed on Sep. 6, 2016, 3 pages.
Munoz-Huerta et al., "A Review of Methods for Sensing the Nitrogen Status in Plants: Advantages, Disadvantages and Recent Advances", dated Aug. 16, 2013, 21 pages.
Metos, "Metos NPK—das Mobile Bodenlabor", dated 2014, 2 pages.
The International Preliminary Examining Authority, "Transmittal of International Preliminary Report on Patentability", in application no. PCT/US2017/060460, dated Feb. 14, 2019, 5 pages.
Examination Report dated Dec. 13, 2021, directed to Australian Application No. 2020281165; 5 pages.
International Search Report and Written Opinion dated Feb. 14, 2018, directed to PCT/US2017/060460; 13 pages.
Kumar, S. et al., "Smart Autonomous Gardening Rover with Plant Recognition using Neural Networks" Procedia Computer Science, 2016. (7 pages).

* cited by examiner

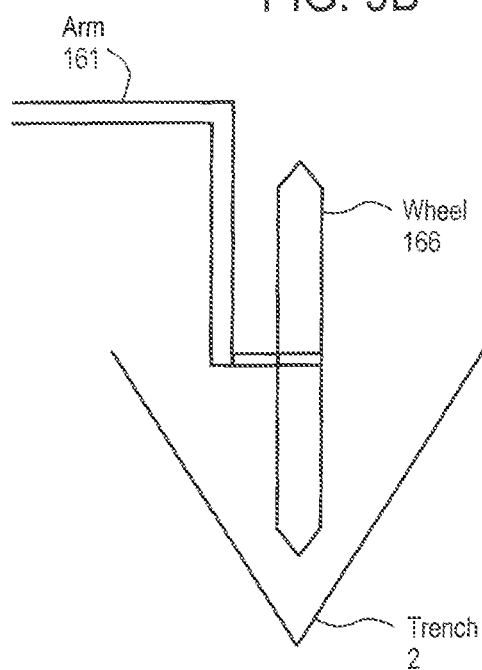

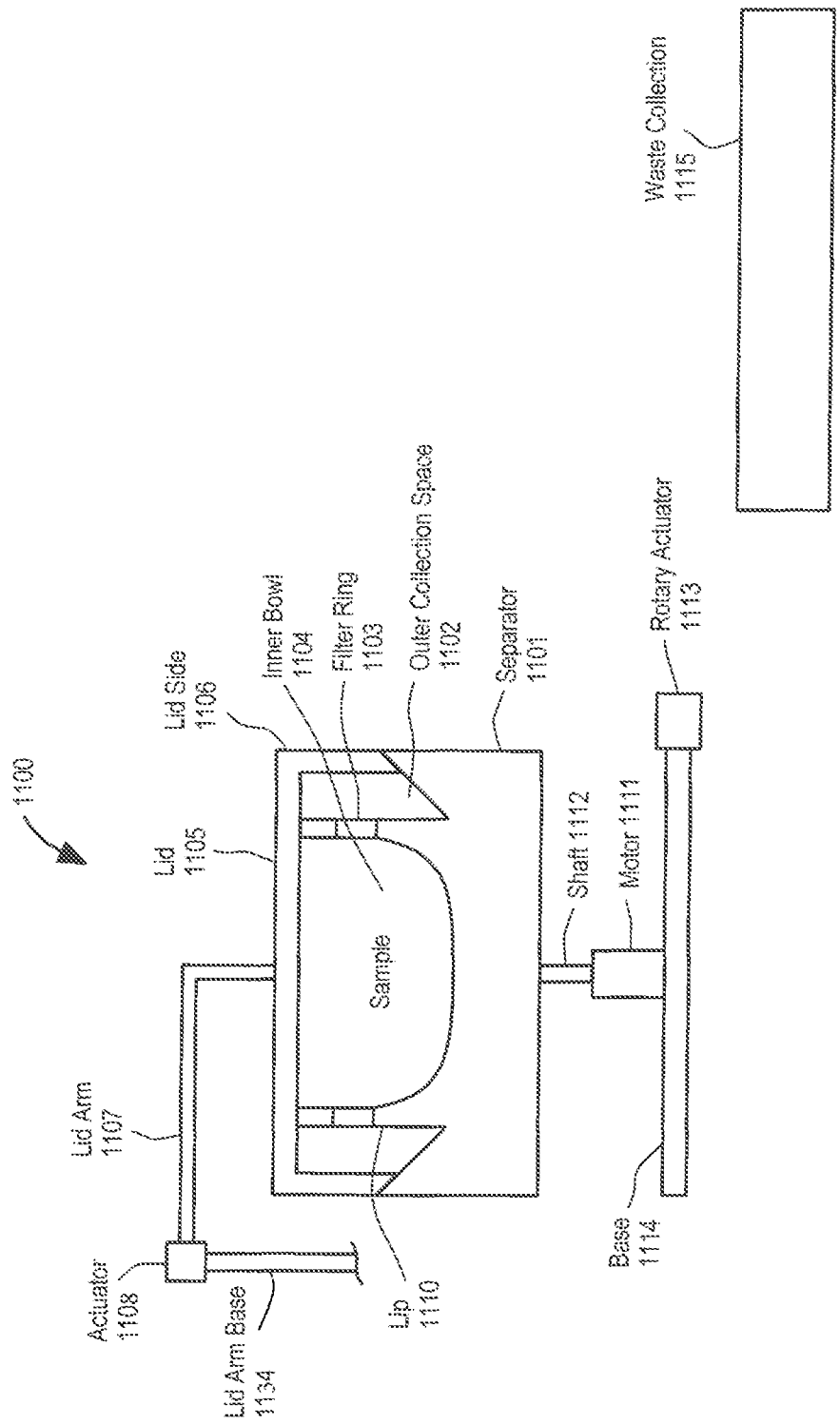

SIDE VIEW

AGRICULTURAL IMPLEMENTS FOR SOIL AND VEGETATION ANALYSIS

BENEFIT CLAIM

This application claims the benefit under 35 U.S.C. § 120 as a Divisional of application Ser. No. 15/806,014, filed Nov. 7, 2017, which claims the benefit under 35 U.S.C. 119(e) of provisional application 62/418,650, filed Nov. 7, 2016, the entire contents of which are hereby incorporated by reference for all purposes as if fully set forth herein. Applicant hereby rescinds any disclaimer of claim scope in the parent applications or the prosecution history thereof and advises the USPTO that the claims in this application may be broader than any claim in the parent applications.

FIELD OF THE DISCLOSURE

Embodiments of the present disclosure relate to implements for measuring properties of soil and/or vegetation.

BACKGROUND

On-the-go soil and/or vegetation sampling is a continuing goal for the agricultural community to understand the amount of nutrients in the field or in vegetation to then determine the amounts of nutrients to be added at points across the field. Knowing the amount of nutrients needed at the different points allows for more efficient application of the nutrients to supply at least the needed amount and to limit over-application.

There are many systems that sample soil and/or vegetation, but these are mainly bag-and-tag systems that collect samples that are then sent to a lab for analysis. There is a delay in receiving the results as the samples need to be shipped and then tested. It would be desirable to be able to test on the go, and in particular with tests that require the soil or vegetation to be in a solution that is tested with a chemical. These types of chemical tests are generally not instantaneous as it takes time to prepare the sample and time for the chemical to react with nutrients in the soil or vegetation to determine the amount of the nutrient. There is a need for a system that can collect and test many samples while on the go across a field.

BRIEF DESCRIPTION OF THE DRAWINGS

In the drawings:

The present disclosure is illustrated by way of example, and not by way of limitation, in the figures of the accompanying drawings and in which:

FIG. 9B illustrates a rear elevation view of an alternative disc for FIG. 9A according to one embodiment.

FIG. 21 illustrates a side sectional view of a separator according to one embodiment.

DETAILED DESCRIPTION

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention. Embodiments are described in sections according to the following outline:
1. SAMPLE COLLECTION APPARATUS
2. SAMPLE PROCESSING APPARATUS
3. SAMPLE TESTING APPARATUS
4. VEHICLE
5. IMPLEMENTATION EXAMPLE—HARDWARE OVERVIEW All references cited herein are hereby incorporated by reference in their entireties. In the event of a conflict in a definition in the present disclosure and that of a cited reference, the present disclosure controls.

Described herein are implements for sensing and/or testing soil and/or vegetation. As described more fully below, sensing is measuring a property of soil and/or vegetation without taking a sample of the soil and/or vegetation for testing.

Examples of sensing include, but are not limited to, spectrographic measurement, electrical conductivity, apparent electrical conductivity, LIDAR, radar, ground penetrating radar, sonar, optical height, camera, time of flight camera. Examples of spectrographic measurement include, but are not limited to, visible light, laser, near-infrared, mid-infrared, infrared, transient infrared spectroscopy, RAMAN spectroscopy, ultraviolet, and x-ray.

1. Sample Collection Apparatus

Figure 1:
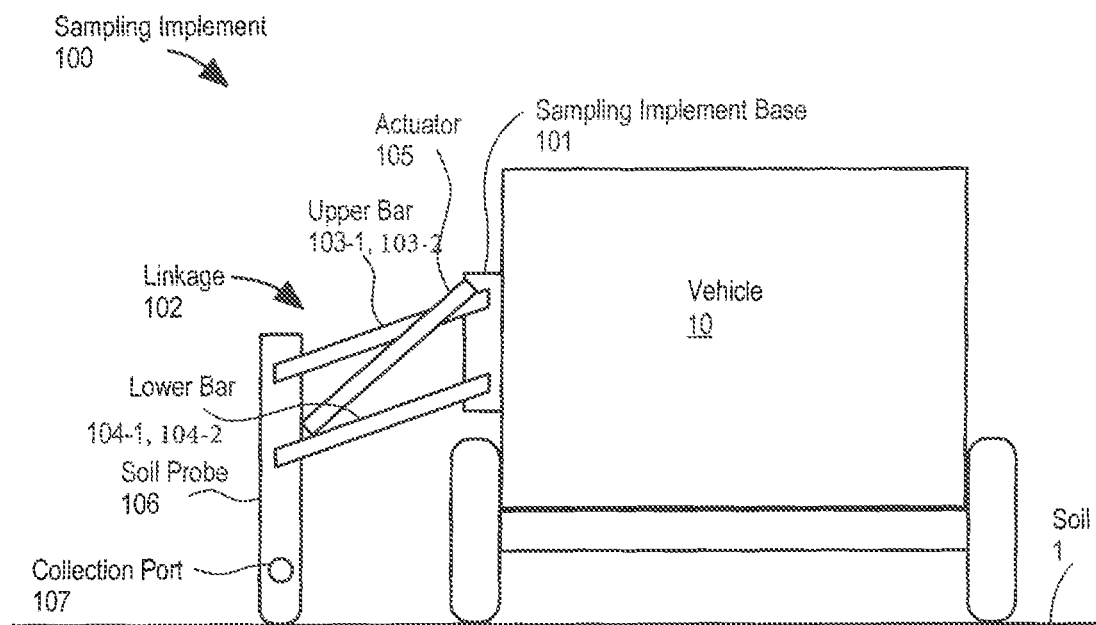
FIG. 1 illustrates a front elevation view of a soil probe on a vehicle according to one embodiment.
Figure 2:
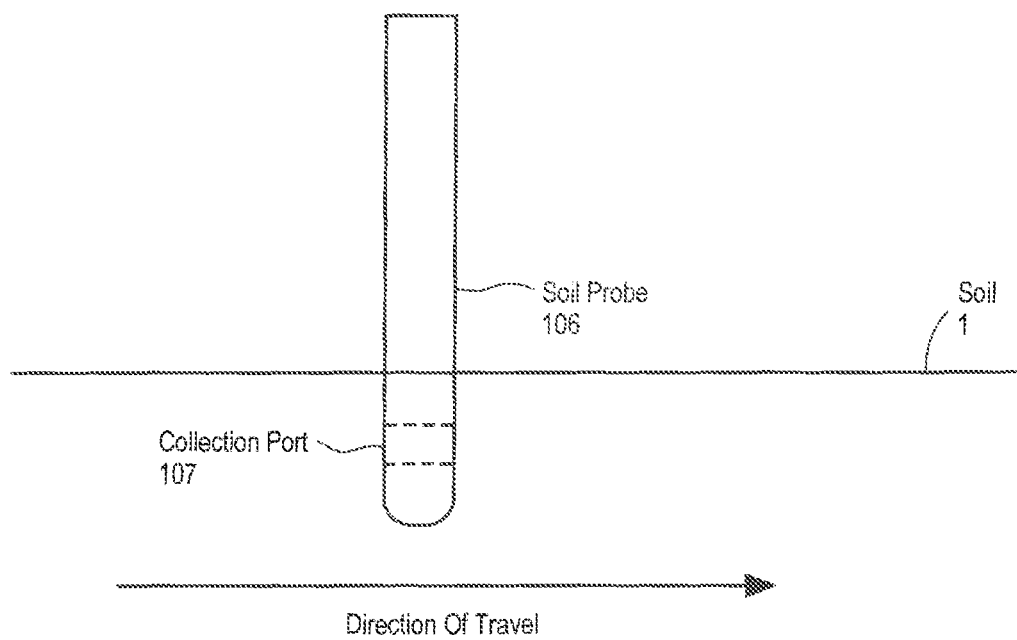
FIG. 2 illustrates a side elevation view of the soil probe from FIG. 1.
Figure 3:
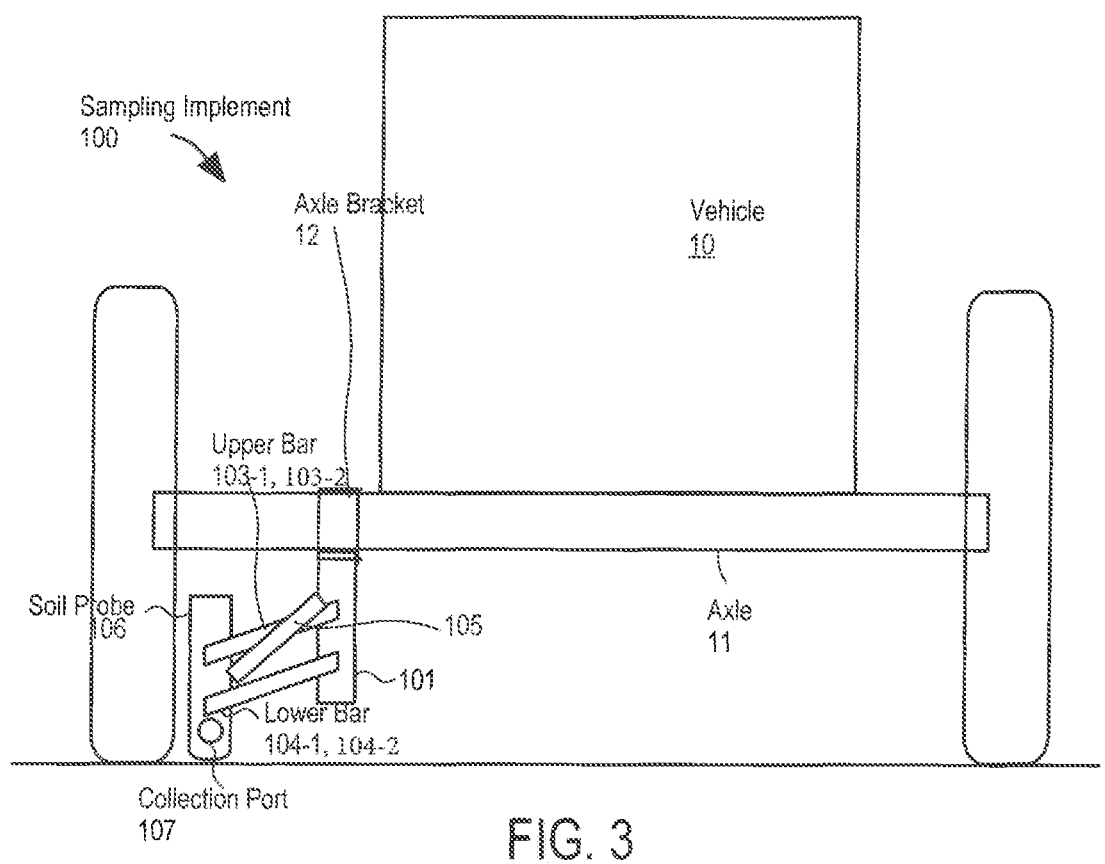
FIG. 3 illustrates a front elevation view of a soil probe mounted to an axle according to one embodiment.
Figure 28:
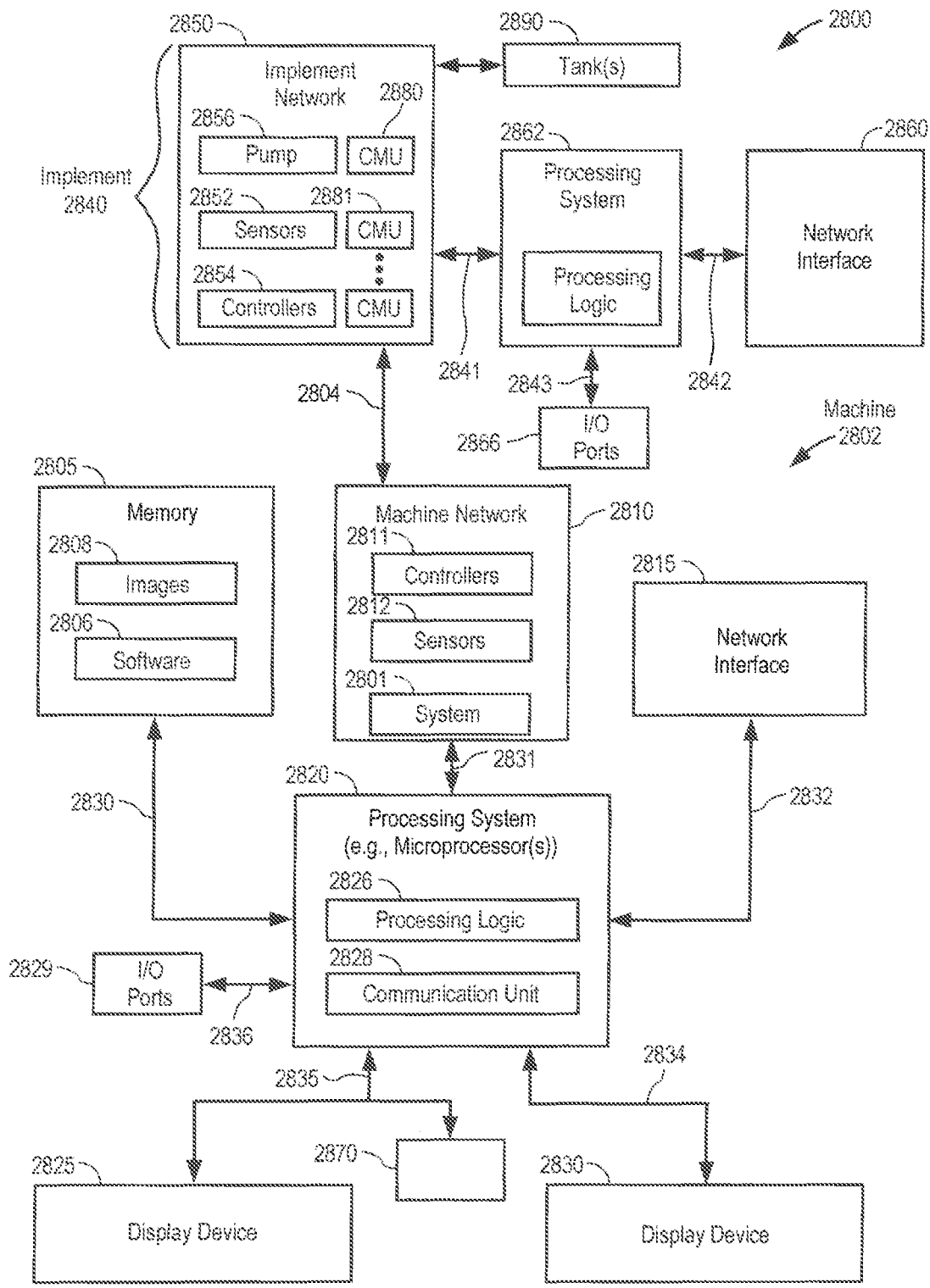
FIG. 28 shows an example of a system 2800 that includes a machine (e.g., vehicle, tractor, combine harvester, etc.) and an implement (e.g., planter, cultivator, plough, sprayer, spreader, irrigation implement, etc.) in accordance with one embodiment.

FIG. 1 illustrates a front elevation view of a soil probe on a vehicle according to one embodiment. FIG. 2 illustrates a side elevation view of the soil probe from FIG. 1. FIG. 3 illustrates a front elevation view of a soil probe mounted to an axle according to one embodiment. FIG. 28 shows an example of a system 2800 that includes a machine (e.g., vehicle, tractor, combine harvester, etc.) and an implement (e.g., planter, cultivator, plough, sprayer, spreader, irrigation implement, etc.) in accordance with one embodiment.

In one embodiment, an agricultural implement 5 includes a vehicle 10 for moving across a field. The vehicle 10 can be any vehicle. In one embodiment, the vehicle 10 is an agricultural vehicle that performs at least one agricultural function including, but not limited to planting, fertilizing, tilling, harvesting. The vehicle 10 is equipped with a sampling implement 100 for sensing and/or sampling at least one of soil and vegetation. The sampling implement 100 is disposed on the vehicle 10 at any location that allows for sensing and/or sampling. In one embodiment as illustrated in FIG. 3, the sampling implement 100 is disposed on a front axle housing 11 (or frame member 11) via axle bracket 12. Disposing sampling implement 100 on front axle housing 11 provides for rigid mounting that does not have significant transverse movement compared to the direction of travel of the vehicle 10. Some vehicles 10 are steered from the rear, which can create transverse motion to the direction of travel. Alternatively, sampling implement 100 can be disposed on vehicle 10 adjacent to axle housing 11 similar to as shown in FIG. 1.

The vehicle 10 includes a location system for determining the position of vehicle 10 on the earth. Location system can be any system that uses signals from a known source for determining position. The location system can be a global positioning system 10001, and the location system can further include a differential global positioning system (DGPS) 10002.

In one embodiment, a map that has field positions is used to send a signal to sampling implement 100 to direct sampling implement 100 to sense and/or sample soil and/or vegetation at each field position in the map as the vehicle 10 traverses a field. The map can be stored in memory 2805 in a central processing unit (CPU) 2820 (e.g., processing system 2820) or memory 2805 that is associated with the CPU. CPU 2820 can be disposed on vehicle 10 or it can be remote from vehicle 10 and in wireless data communication with sampling implement 100.

The map that is used to indicate where to sense or take a sample can be any map that has information about the field that was previously measured. Examples of maps include, but are not limited to, yield, moisture, soil nutrient content, pH, organic matter content, electrical conductivity, soil compaction, elevation, drainage, and NDVI (normalized difference vegetation index). Soil nutrients include, but are not limited to, nitrogen, phosphorus, potassium, calcium, sulfur, magnesium, zinc, manganese, boron, chlorine, copper, iron, and molybdenum. Points in the field for sensing and/or sampling can be selected based on points in the field that had high, average, low measurements, or combinations thereof for the characteristic measured. These maps are not based on geo selection such that the points are chosen to evenly sample a field. The points are chosen based on the previously tested values.

In one embodiment, disclosed is an agricultural implement 5 that includes vehicle, a collection system, and a testing system. Additionally, if needed, a processing system can be further included to process the samples prior to testing.

In one embodiment shown in FIG. 1, FIG. 2, FIG. 3, FIG. 4, FIG. 5, FIG. 6, FIG. 7A, FIG. 7B, FIG. 7C, FIG. 7D, FIG. 8, a collection system is a probe collection system. The probe collection system is attached to the vehicle 10, and it has a four-bar linkage 102 with upper bars 103-1, 103-2 and lower bars 104-1, 104-2 attached at their first ends to vehicle 10 and connected to a soil probe 106 at their second ends to an upper end of soil probe 106. At a lower end of soil probe 106, there is a collection port extending through soil probe 106 along a direction of travel of vehicle 10. To drive soil probe 106 into the soil and withdraw soil probe 106, an actuator 105 is disposed between soil probe 106 and vehicle 10. A signal from CPU 2820 is sent to actuator 105 to lower soil probe 106. Once in the soil, soil probe 106 is pulled downward by the contact with the soil. When a sample has been taken, CPU 2820 sends a signal to actuator 105 to raise soil probe 106. Also, the position of the sample is stored in memory 2805.

Figure 4:
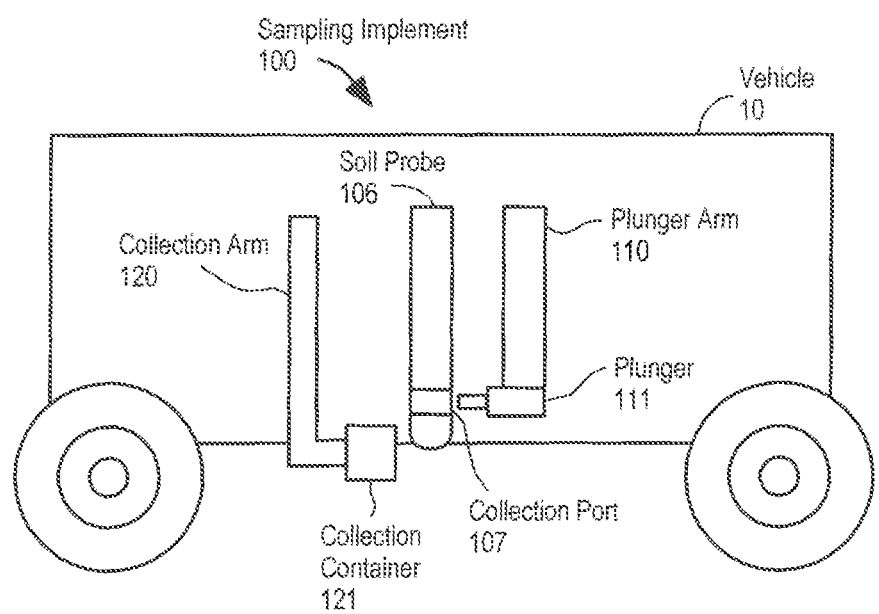
FIG. 4 illustrates a side elevation view of a soil probe on a vehicle according to one embodiment.
Figure 5:
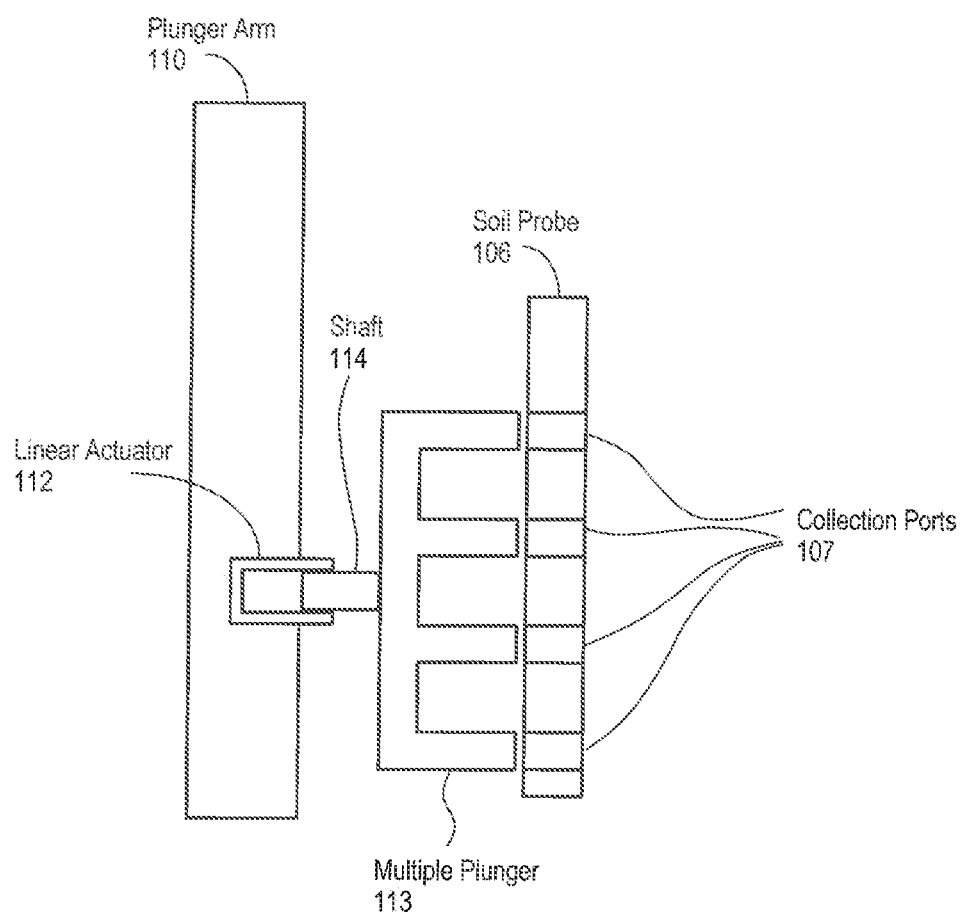
FIG. 5 illustrates a side elevation view of a soil probe and multiple plunger according to one embodiment.
Figure 6:
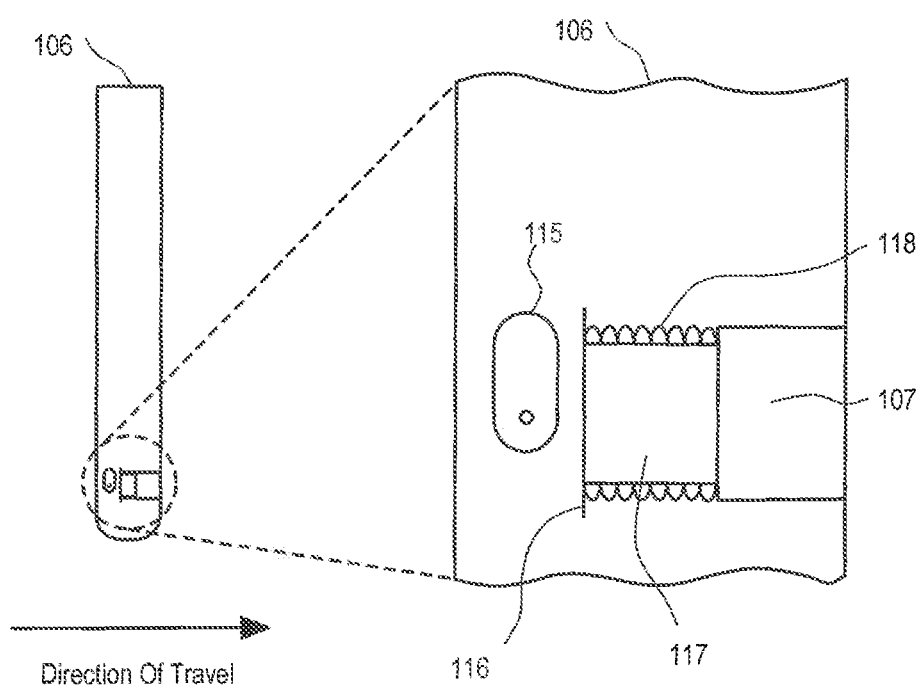
FIG. 6 illustrates a side sectional view of a soil probe according to one embodiment.

FIG. 4 illustrates a side elevation view of a soil probe on a vehicle according to one embodiment. FIG. 5 illustrates a side elevation view of a soil probe and multiple plunger according to one embodiment. FIG. 6 illustrates a side sectional view of a soil probe according to one embodiment.

In some embodiments, a plunger 111 on plunger arm 110 attached to vehicle 10 receives a signal from CPU 2820 to move to soil probe 106 and align plunger 111 with collection port 107. A signal from CPU 2820 causes plunger 111 to extend into collection port 107 and eject the sample from the collection port 107. Waiting for the sample is collection container 121, which is attached to collection arm 120, which is attached to vehicle 10. Prior to the plunger ejecting the sample, CPU 2820 sends a signal to collection arm 120 to move collection container 121 to a position adjacent to the collection port 107 opposite of the plunger 111. After the sample has been delivered to collection container 121, collection arm 120 is actuated to move collection container 121 to a processing system described below.

In an alternative embodiment shown in FIG. 6, the plunger 111 in not attached to plunger arm 110. Plunger 117 is in soil probe 106 adjacent to collection port 107. Soil probe 106 has a plunger lip 116 disposed on plunger 117 opposite the side of the collection port 107. Plunger lip 116 has a diameter greater than plunger 117 such that a biasing member 118 (such as a spring) is disposed between plunger lip 116 and collection port 107 to keep plunger 117 retracted and collection port 107 open. Disposed behind plunger 117 opposite of collection port 107 is a cam 115. Cam 115 when rotated will cause plunger 117 to extend into collection port 107 to eject the sample. Cam 115 is in communication with CPU 2820 to receive signals to actuate when samples need to be ejected. In another embodiment (not shown), biasing member 118 need not be included. The force from soil entering collection port 107 will cause plunger 117 to retract along with cam 115 being commanded by CPU 2820 to allow plunger 117 to not be in collection port 107.

In another embodiment shown in FIG. 5, soil probe 106 can have multiple collection ports 107. To eject samples, a multiple plunger 113 having a shaft 114 is driven by a linear actuator 112, which is attached to plunger arm 110. Linear actuator 112 is in communication with CPU 2820 to allow multiple plunger 113 to enter then withdraw from the collection ports 107.

Figure 7A:
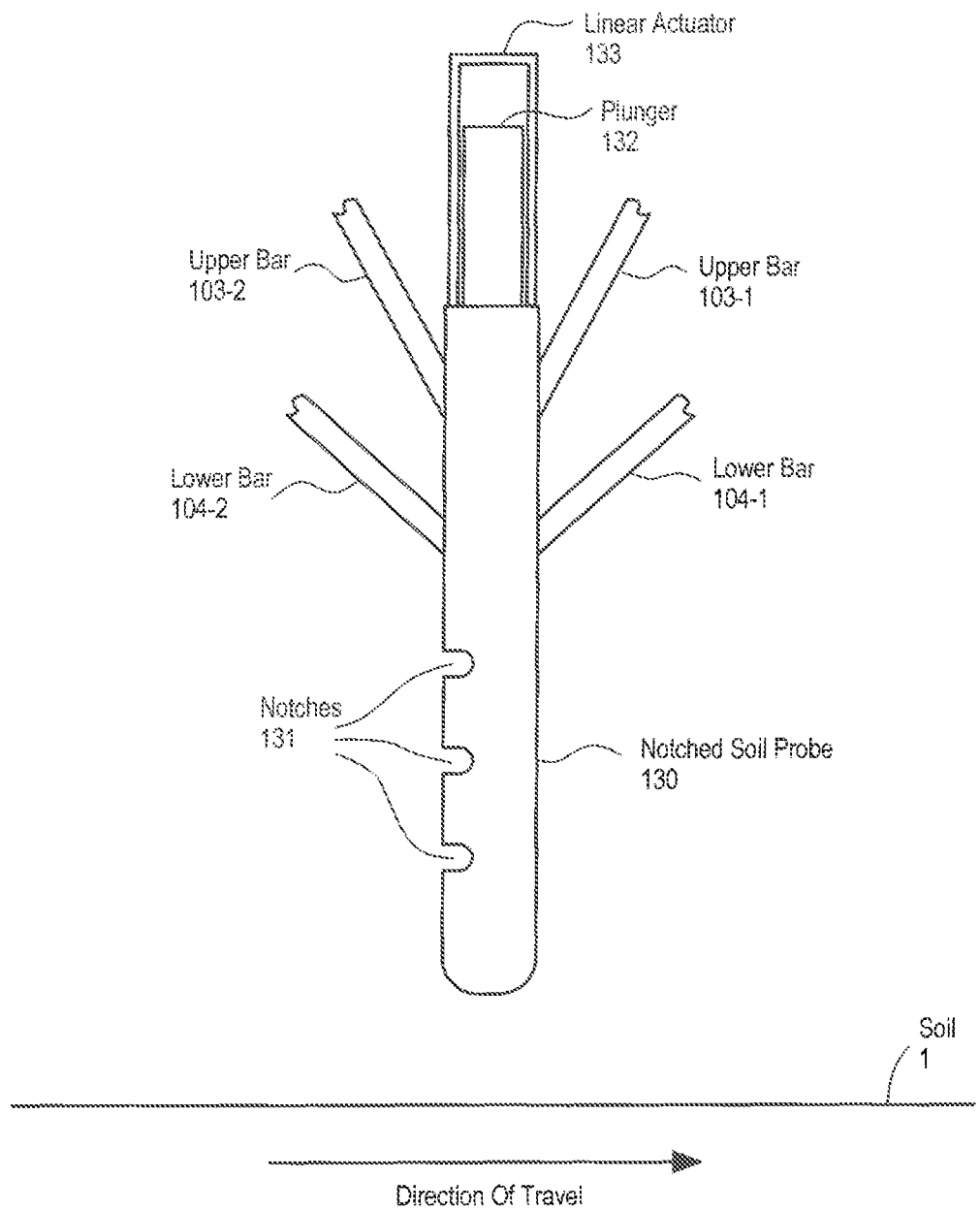
FIG. 7A illustrates a side elevation view of a soil probe according to one embodiment.
Figure 7C:
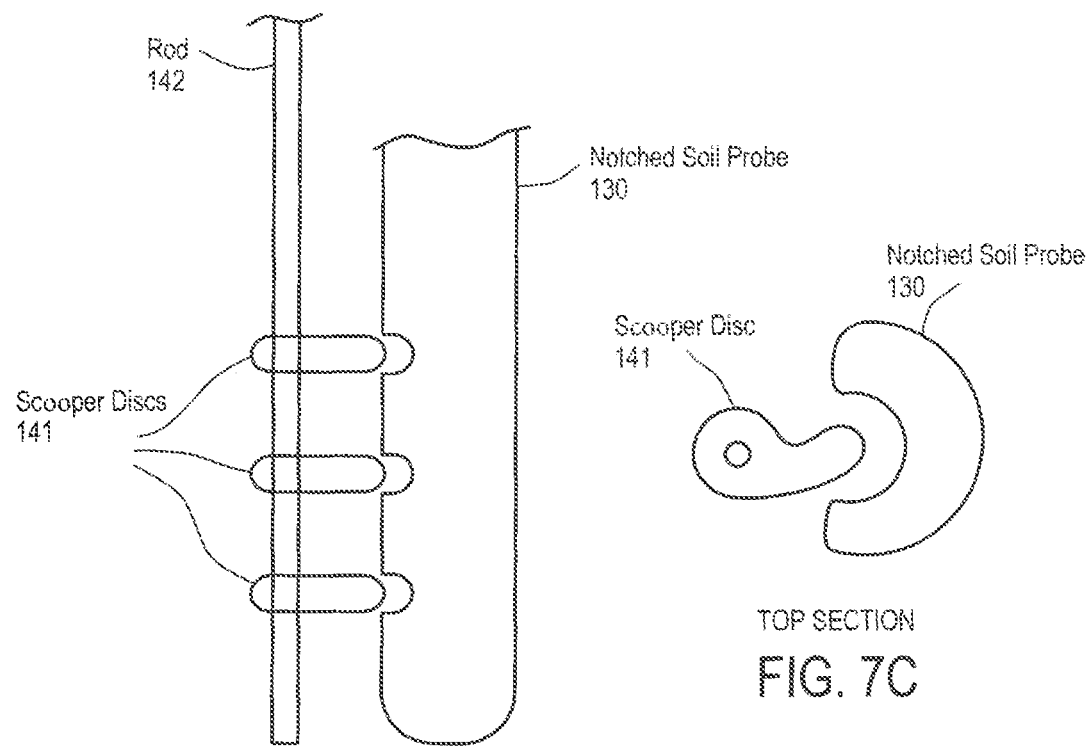
FIG. 7C is a top sectional view of the soil probe of FIG. 7B with the scooper disc according to one embodiment.
Figure 7B:
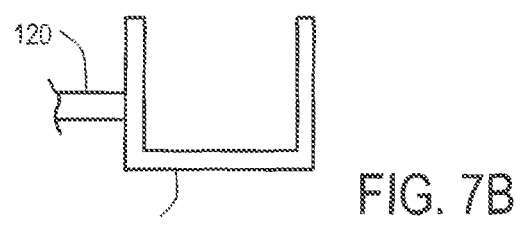
FIG. 7B illustrates side elevation view of the soil probe of FIG. 7A with rod with scooper discs according to one embodiment.
Figure 7D:
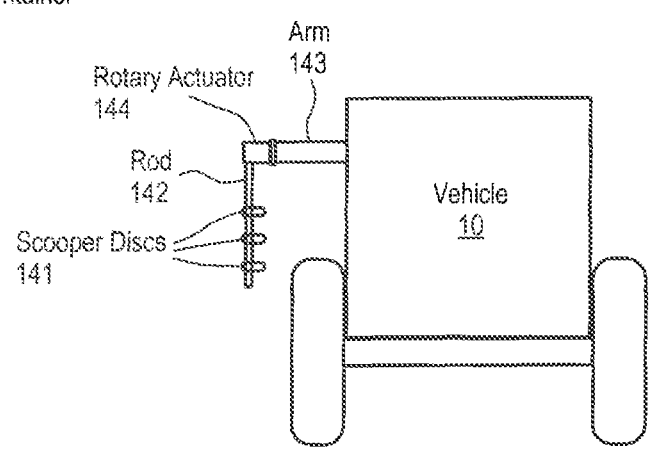
FIG. 7D illustrates a front elevation view of the soil probe and rod with scooper discs of FIG. 7B on a vehicle according to one embodiment.

FIG. 7A illustrates a side elevation view of a soil probe according to one embodiment. FIG. 7B illustrates side elevation view of the soil probe of FIG. 7A with rod with scooper discs according to one embodiment. FIG. 7C is a top sectional view of the soil probe of FIG. 7B with the scooper disc according to one embodiment. FIG. 7D illustrates a front elevation view of the soil probe and rod with scooper discs of FIG. 7B on a vehicle according to one embodiment.

In another embodiment as shown in FIG. 7A, FIG. 7B, FIG. 7C, FIG. 7D, a notched soil probe 130 replaces soil probe 106 as in FIG. 1 with notched soil probe 130 connected to upper bars 103-1, 103-2 and lower bars 104-1, 104-2. Notched soil probe 130 has notches 131 on a side rearward of a direction of travel. Notched soil probe 130 is plunged into soil by actuator 133 to collect soil inside of notched soil probe 130 and then withdraw. There will be soil exposed in notches 131. Disposed adjacent to notched soil probe 130 is a rod 142 having scooper discs 141 that align with the notches 131. Rod 142 is attached to vehicle 10 through a rotary actuator 144, which allows rotation of rod 142 to allow scooper discs 141 to scoop soil from notches 131. Rod actuator 144 is attached to rod arm 143, which is attached to vehicle 10. Rotary actuator 144 is in communication with CPU 2820 to receive signals to cause rotary actuator 144 to rotate. Soil is removed from notches 131 and falls under gravity to collection container 121 (described above). After soil is removed from notches 131, there is a plunger 132 disposed within notched soil probe 130 at the top of notched soil probe 130 and is actuated by linear actuator 133, which is in communication with CPU 2820. Linear actuator 133 receives a signal from CPU 2820 to extend plunger 132 into notched soil probe 130 to expel soil out of notched soil probe 130.

Figure 8:
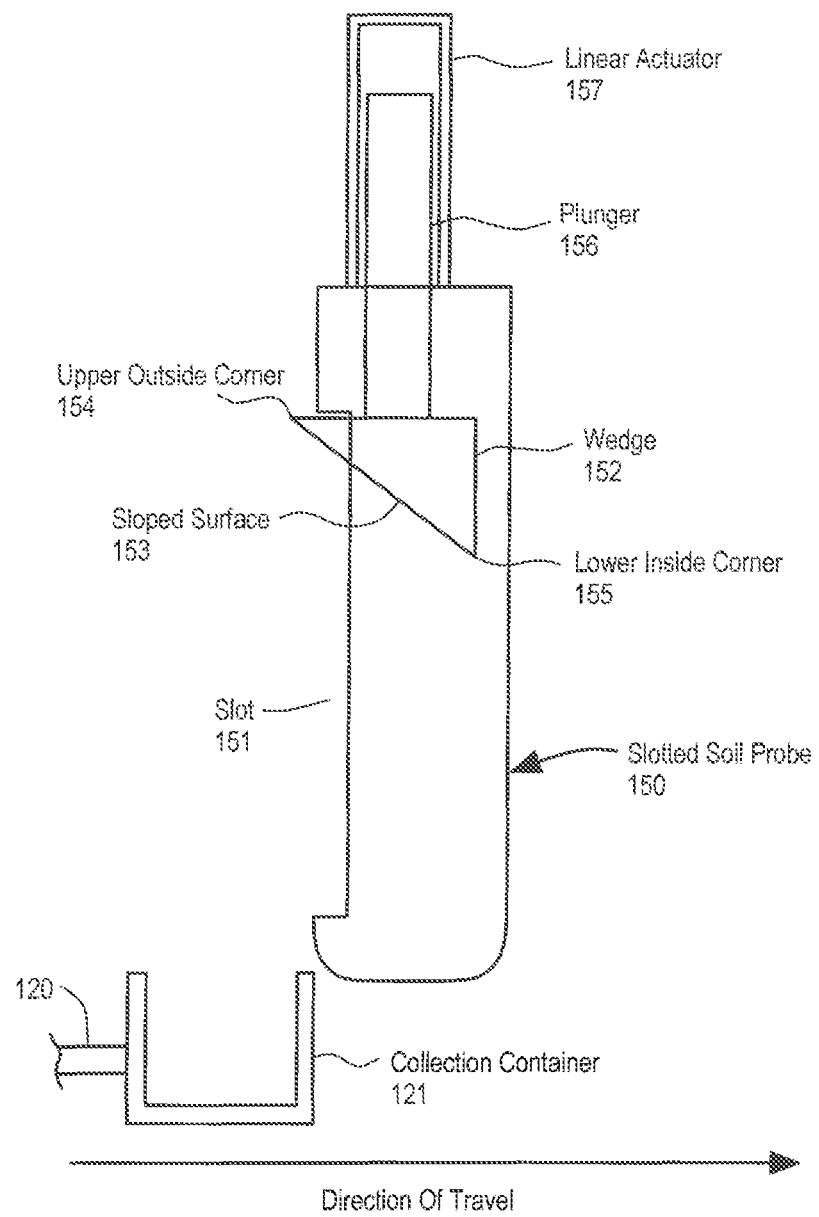
FIG. 8 illustrates a side elevation view of a soil probe according to one embodiment.

FIG. 8 illustrates a side elevation view of a soil probe according to one embodiment.

In another embodiment as shown in FIG. 8, notched soil probe 130 is replaced with slotted soil probe 150. This embodiment eliminates the need to use rod 142 and scooper discs 141. Slotted soil probe 150 has a slot 151 rearward of a direction of travel. Plunger 156 further has a wedge 152 disposed on its end. Wedge 152 extends the full inner diameter of slotted soil probe 150 and has a sloped surface 153 from top outside corner 154 to lower inside corner 155. When slotted soil probe 150 is withdrawn from the soil, linear actuator 157 receives a signal from CPU 2820 to extend plunger 156 and wedge 152 down through slotted soil probe 150. The soil within slot 151 falls under gravity into collection container 121 (as described above).

Figure 9A:
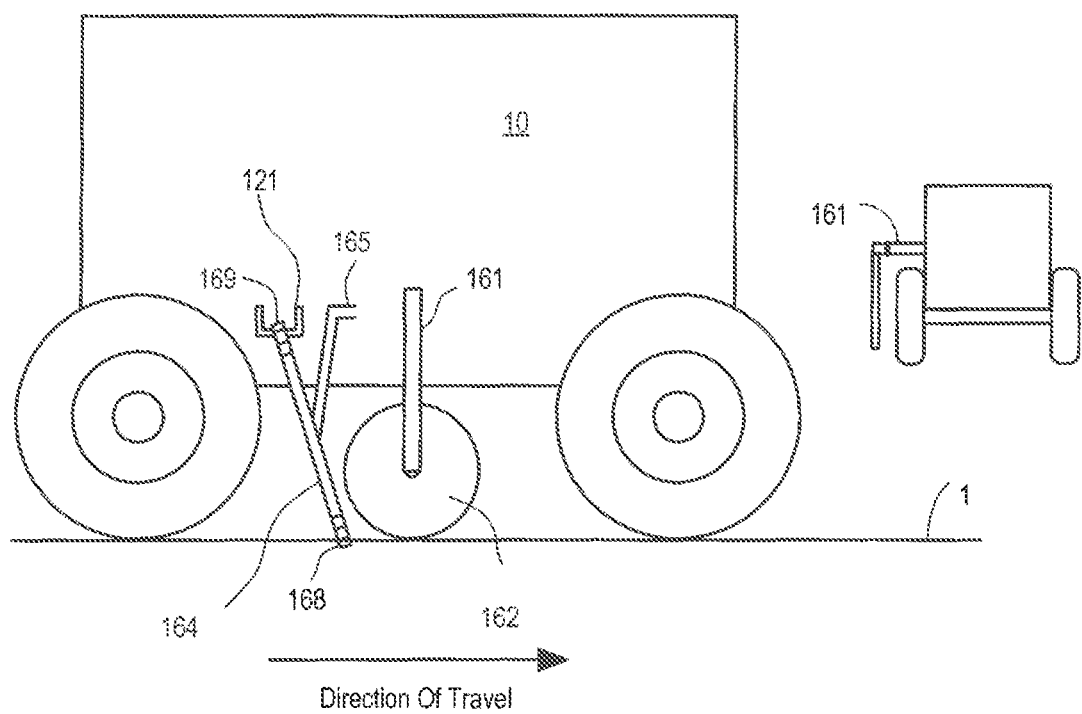
FIG. 9A illustrates a side elevation view of a vehicle with a disc and auger collection system according to one embodiment.

FIG. 9A illustrates a side elevation view of a vehicle with a disc and auger collection system according to one embodiment. FIG. 9B illustrates a rear elevation view of an alternative disc for FIG. 9A according to one embodiment.

In another embodiment as shown in FIGS. 9A and 9B, a collection system is a disc and auger collection system. Disc 162 is connected to vehicle 10 by arm 161. In one embodiment, disc 162 is offset from vertical. As disc 162 rotates, a trench 2 is formed in soil 1. An auger 164 is connected to the vehicle, and auger 164 has a soil entrance end 168 that extends into trench 2 for collecting soil. The soil is transported up the auger to a soil exit end 169 and then dispensed into collection container 121. Auger 164 is in data communication with CPU 2820, which commands auger 164 to actuate to collect soil. After soil is collected in collection container 121, auger 164 can be raised out of trench 2 and commanded to actuate to empty auger 164 of soil.

In an alternative embodiment as shown in FIG. 9B, a disc collection system is shown. Cutter disc 166 is connected to vehicle 10 by arm 161. Cutter disc 166 is tapered along its radial edge. As cutter disc 166 rotates, a trench 2 is formed in soil 1. An auger 164 is connected to the vehicle, and auger 164 has a soil entrance end 168 that extends into trench 2 for collecting soil. The soil is transported up the auger to a soil exit end 169 and then dispensed into collection container 121. Auger 164 is in data communication with CPU 2820, which commands auger 164 to actuate to collect soil. After soil is collected in collection container 121, auger 164 can be raised out of trench 2 and commanded to actuate to empty auger 164 of soil.

Figure 10A:
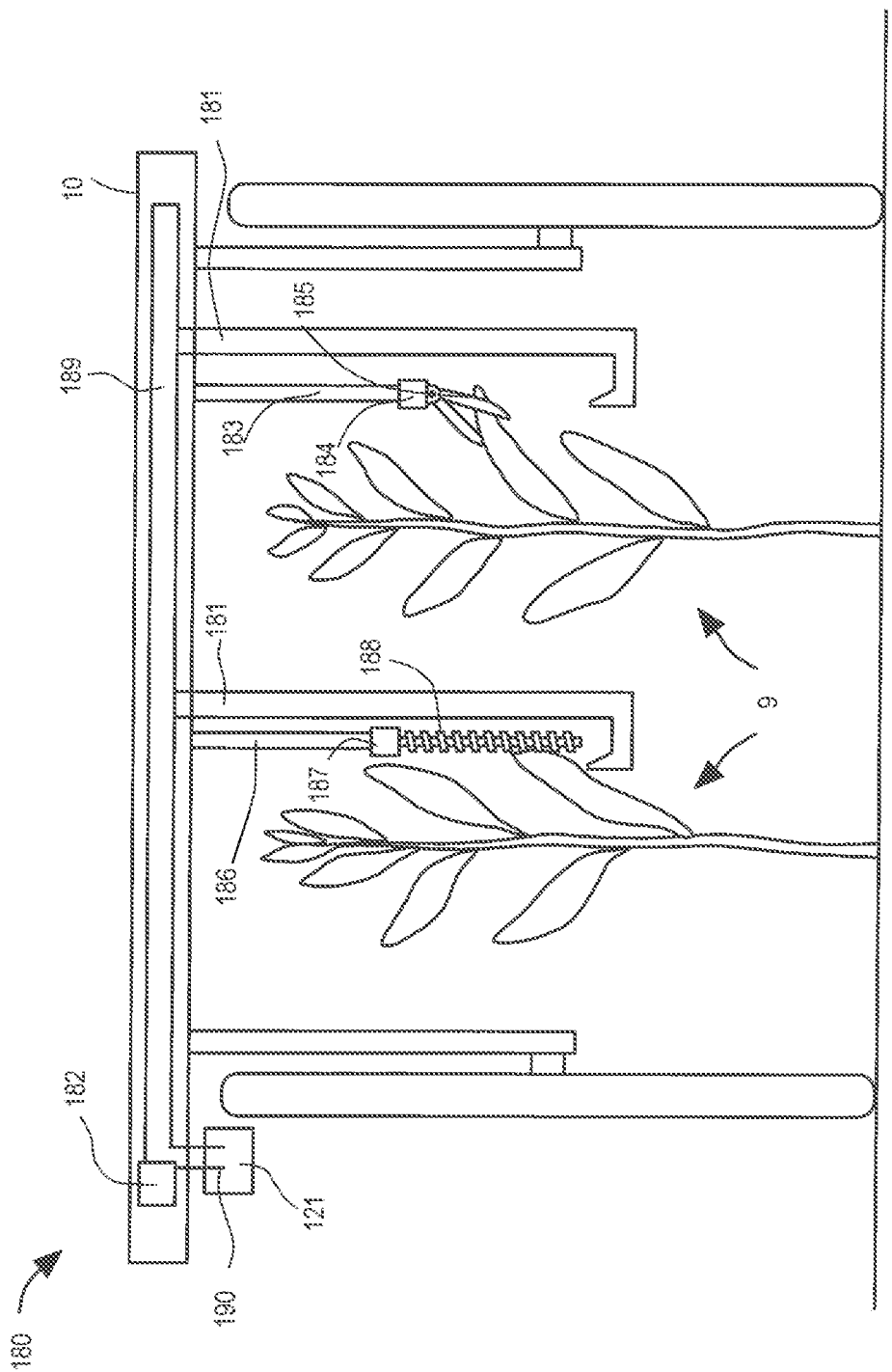
FIG. 10A illustrates a front elevation view of a vegetation collection system according to one embodiment.
Figure 10B:
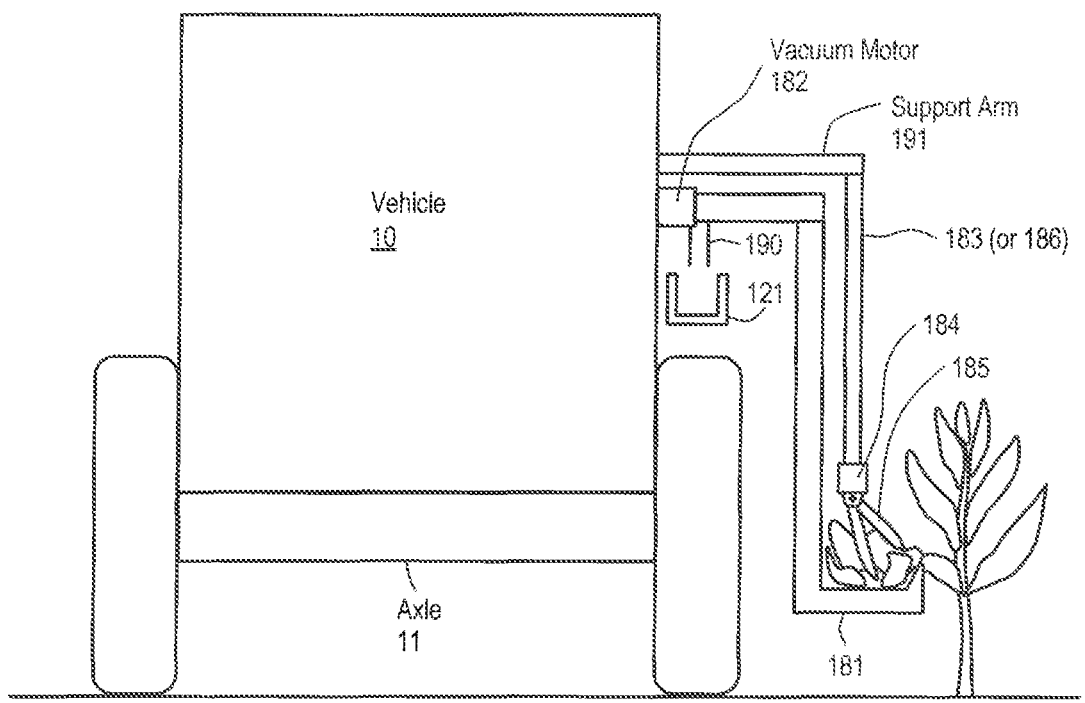
FIG. 10B illustrates a front elevation view of a vegetation collection system according to one embodiment.
Figure 10C:
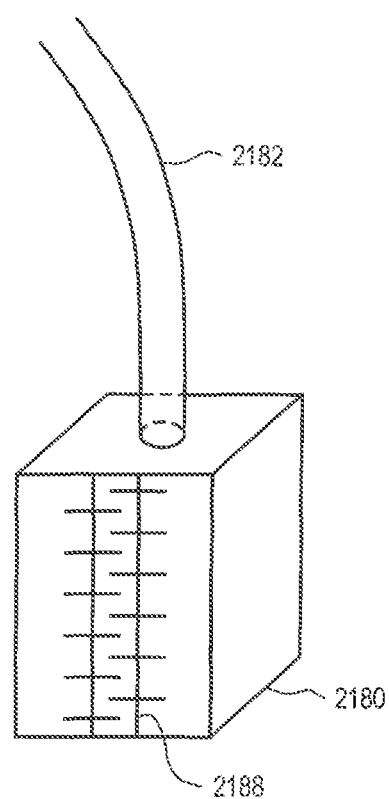
FIG. 10C illustrates a perspective view of a vegetation collection system according to one embodiment.

FIG. 10A illustrates a front elevation view of a vegetation collection system according to one embodiment. FIG. 10B illustrates a front elevation view of a vegetation collection system according to one embodiment. FIG. 10C illustrates a perspective view of a vegetation collection system according to one embodiment.

As illustrated in FIG. 10A, vegetation collection system 180 cuts and collects vegetation. FIG. 10A illustrates two separate embodiments. Both embodiments have a main vacuum line 189 in communication with a vacuum motor 182 and a vacuum tube exit 190. In both of these embodiments, the vehicle 10 passes over the vegetation to be collected. Main vacuum line 189 has a vacuum tube 181 extending down from the main vacuum line 189 and ending proximate to a cutter (scissors 185 or sickle 188). In one embodiment, a sickle arm 186 is disposed under vehicle 10 and extends downward. A motor 187 is disposed at the end of sickle arm 186 and is connected to sickle 188. Motor 187 is in communication with CPU 2820 to receive signals to actuate to drive sickle 188. In the other embodiment, a scissor arm 183 is disposed under vehicle 10 and extends downward. An actuator 184 is disposed at the end of scissor arm 183 and is connected to scissors 185. Actuator 184 is in communication with CPU 2820 to receive signals to actuate scissors 185.

In an alternative embodiment illustrated in FIG. 10B, the vegetation collection system 180 is disposed on the side of vehicle 10. Support arm 191 is disposed on the side of vehicle 10 projecting out from vehicle 10. Scissor arm 183 (or sickle arm 186) is then disposed at the end of support arm 191. Either of the above embodiments for sickle 188 or scissors 185 can be used in this embodiment.

Another embodiment that can be used with either embodiment shown in FIG. 10A or 10B is illustrated in FIG. 10C. This embodiment is similar to the device described in U.S. Pat. No. 5,142,786. A body 2180 has a sickle 2188 disposed on an opening on a side of body 2180. A vacuum hose 2182 is attached to body 2180 to pull clippings through hose 2182 for collection. Vacuum pulls vegetation into body 2180 where sickle 2188 cuts the vegetation.

The sample when taken is associated with a location by a location system. The sample with its specific location is stored in memory 2805, and tracked by CPU 2820 as the sample transfers from one system to the next system such that results from testing are associated with the location tested.

Figure 27A:
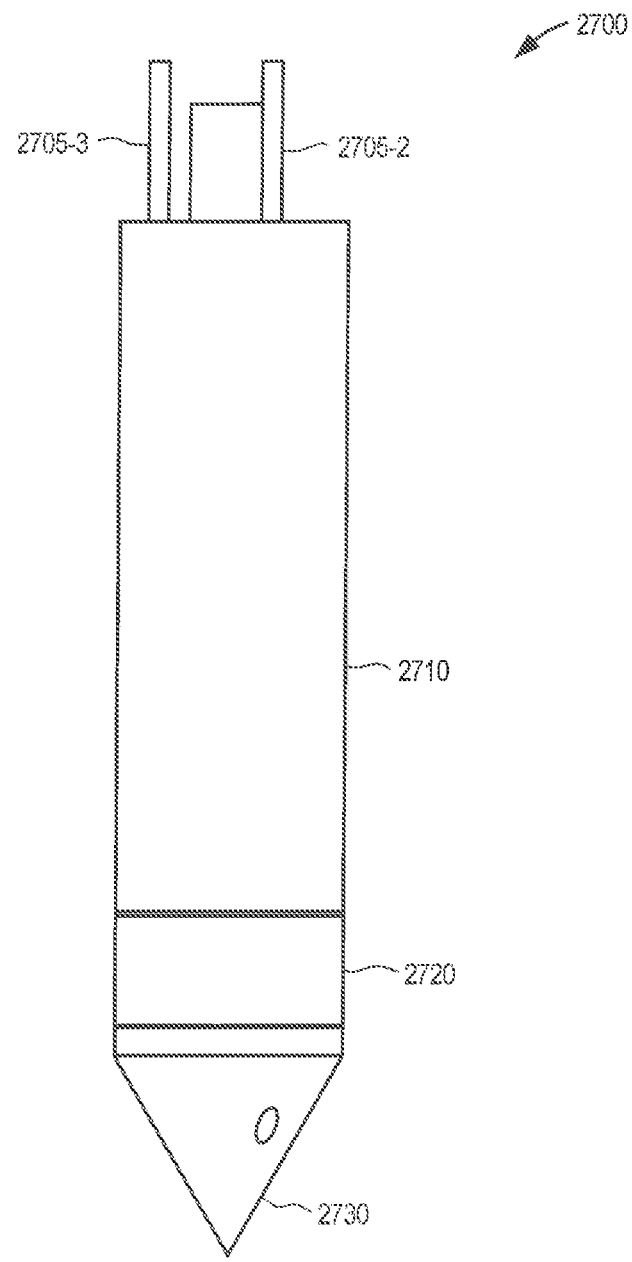
FIG. 27A illustrates a side view of a sample probe according to one embodiment.
Figure 27B:
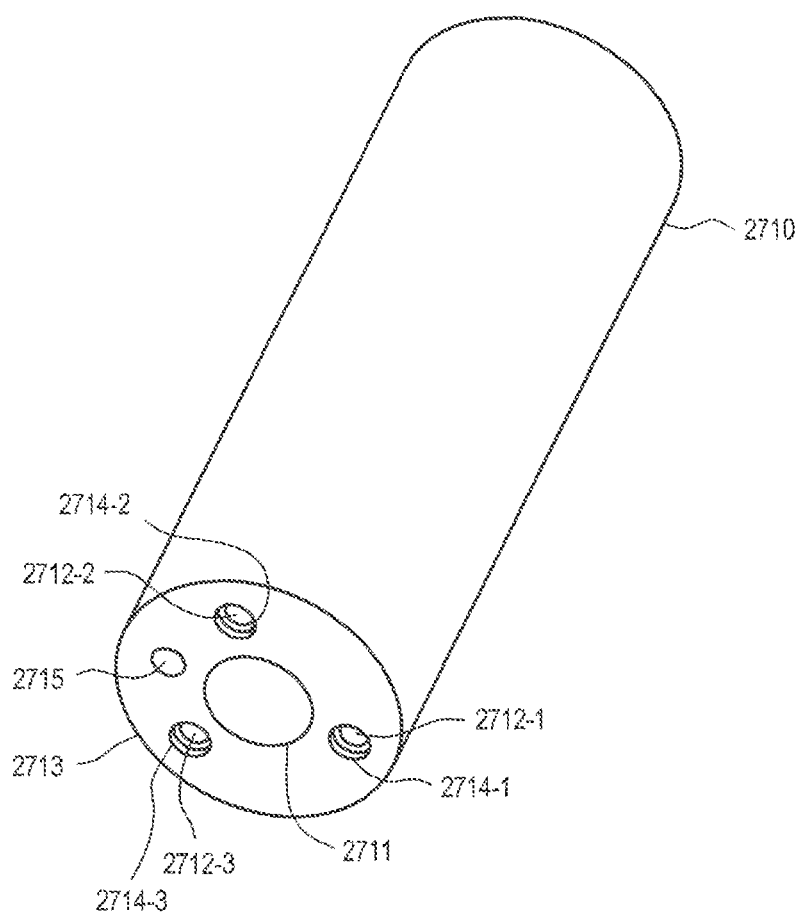
FIG. 27B illustrates a perspective view of a first body of the sample probe of FIG. 27A.
Figure 27C:
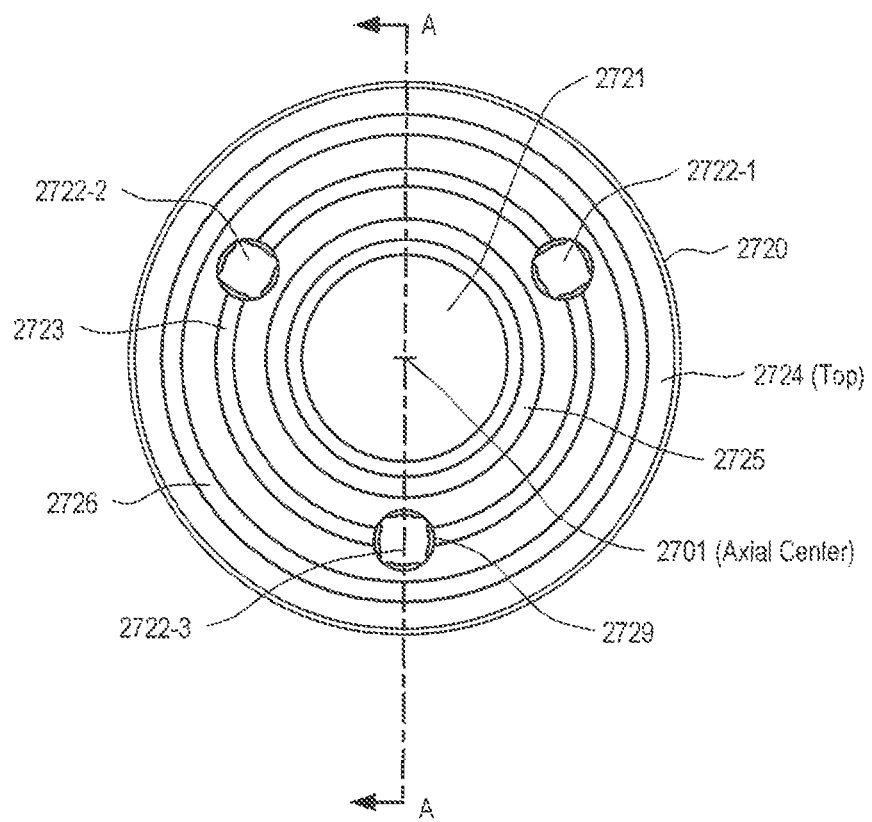
FIG. 27C illustrates a top view of the second body of the sample probe of FIG. 27A.
Figure 27D:
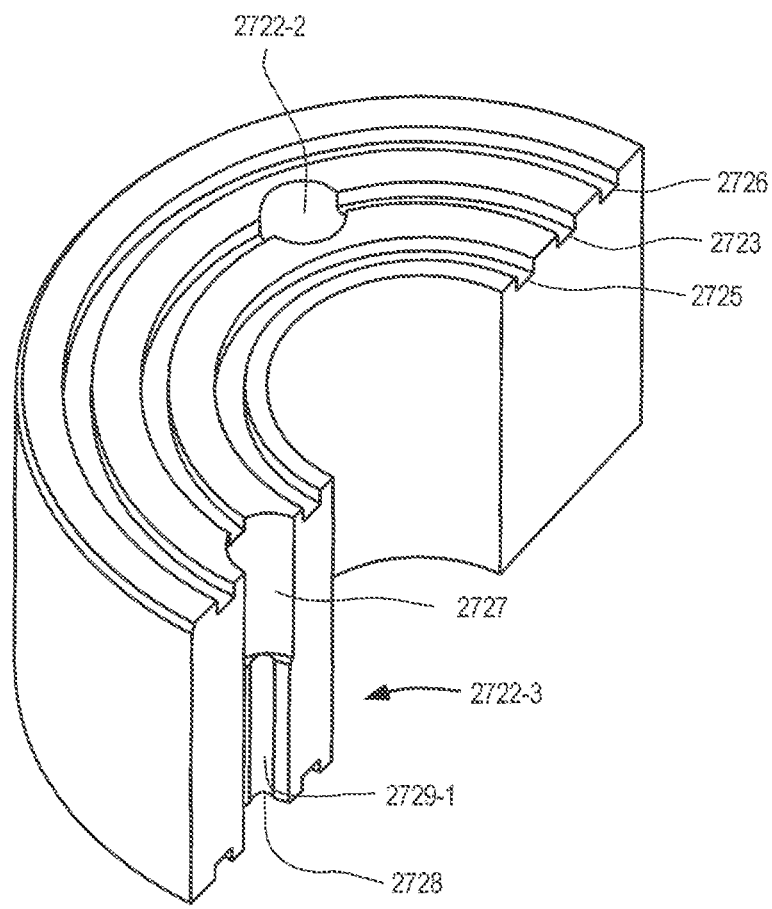
FIG. 27D illustrates a top perspective section view of the second body of the sample probe of FIG. 27A taken along line A-A.
Figure 27E:
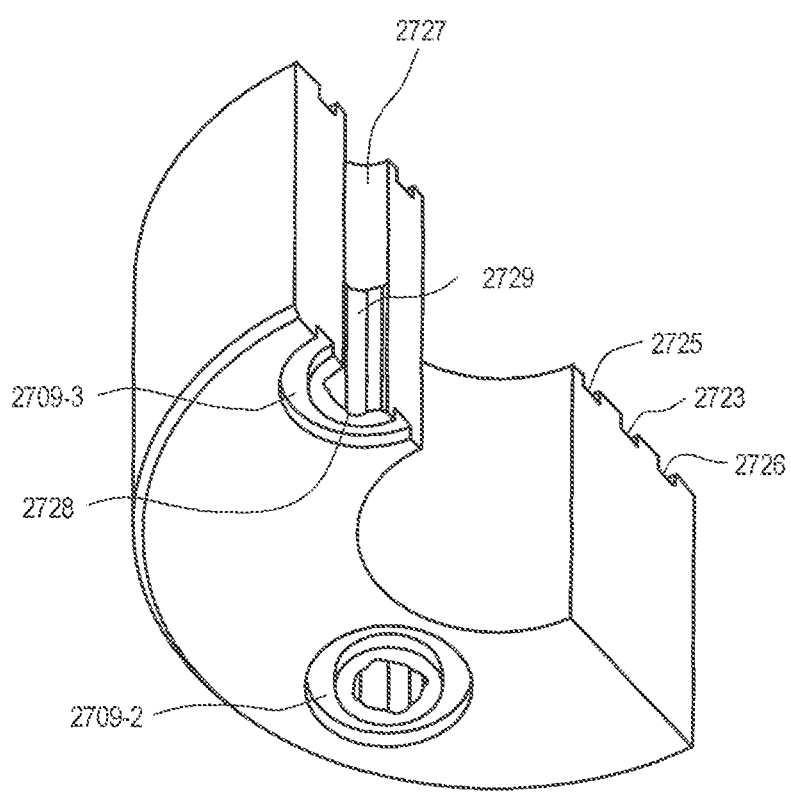
FIG. 27E illustrates a bottom perspective section view of the second body of the sample probe of FIG. 27A taken along line A-A
Figure 27F:
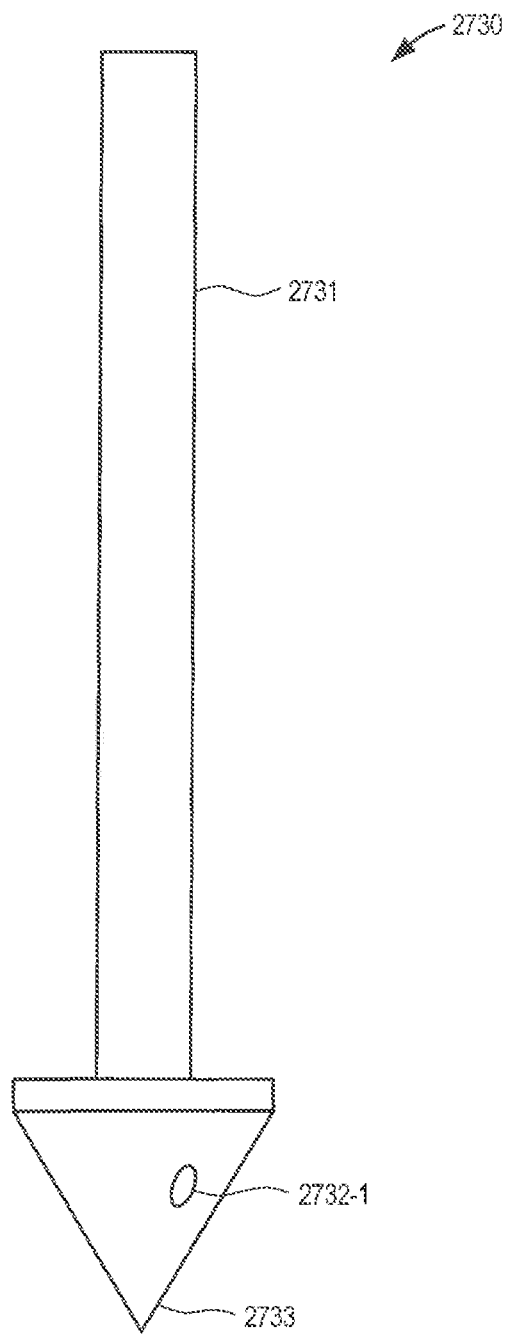
FIG. 27F illustrates a perspective view of the central body of the sample probe of FIG. 27A.
Figure 27G:
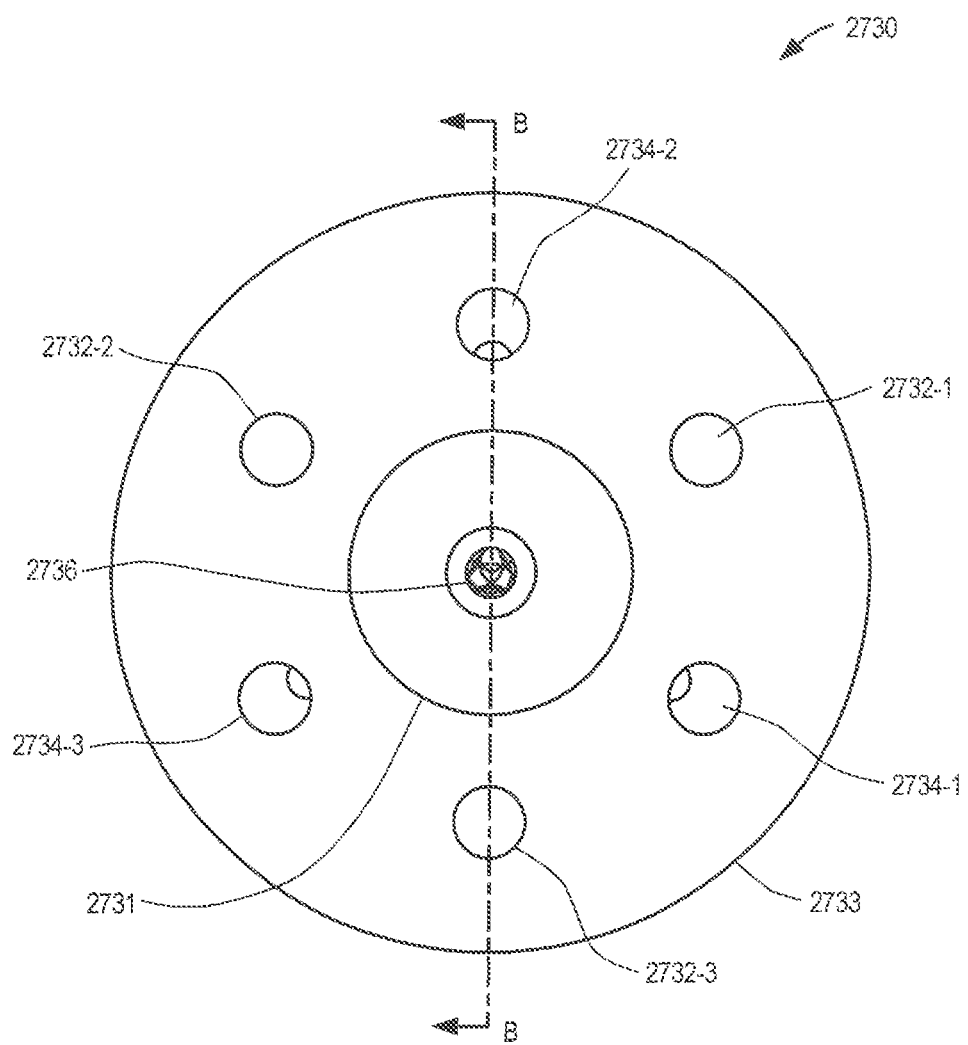
FIG. 27G illustrates a top view of the central body of the sample probe of FIG. 27A.
Figure 27H:
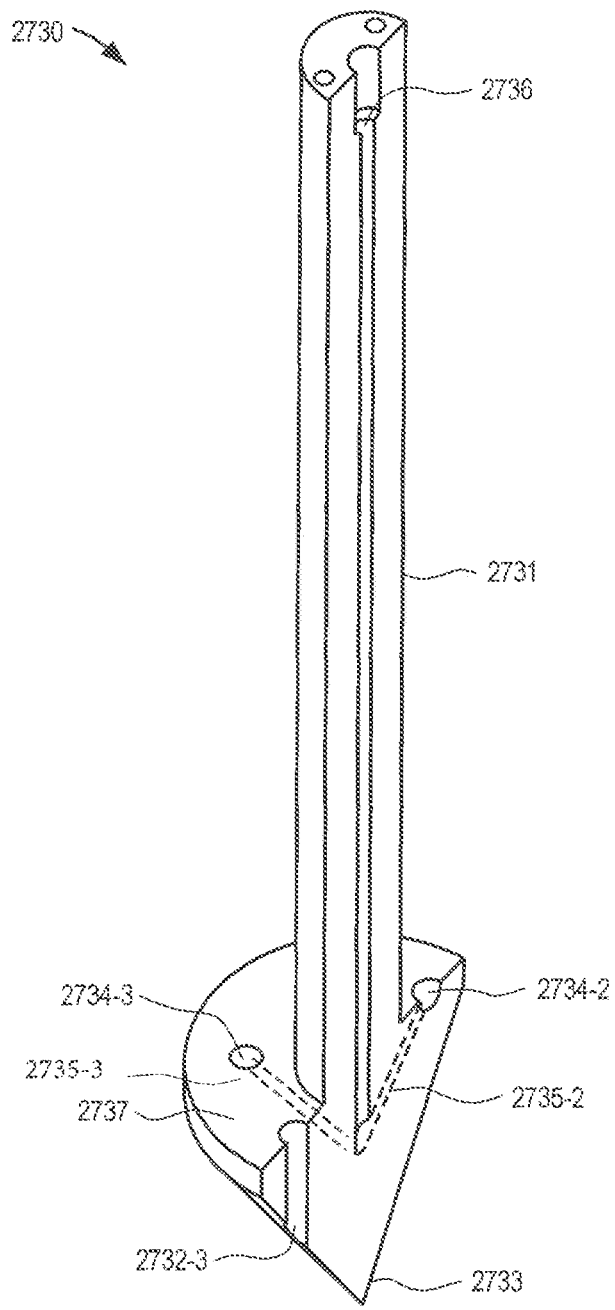
FIG. 27H illustrates a perspective section view of the central body of FIG. 27A taken along line B-B.

FIG. 27A illustrates a side view of a sample probe according to one embodiment. FIG. 27B illustrates a perspective view of a first body of the sample probe of FIG. 27A. FIG. 27C illustrates a top view of the second body of the sample probe of FIG. 27A. FIG. 27D illustrates a top perspective section view of the second body of the sample probe of FIG. 27A taken along line A-A. FIG. 27E illustrates a bottom perspective section view of the second body of the sample probe of FIG. 27A taken along line A-A. FIG. 27F illustrates a perspective view of the central body of the sample probe of FIG. 27A. FIG. 27G illustrates a top view of the central body of the sample probe of FIG. 27A. FIG. 27H illustrates a perspective section view of the central body of FIG. 27A taken along line B-B.

A sample probe according to another embodiment is illustrated in FIG. 27A. Sample probe 2700 allows for the collection of solid soil, fluidization of the solid soil, and then pumping of the fluidized sample. This simplifies the system by eliminating mechanical transfer of samples from soil probes to other parts of the system. Sample probe 2700 has three components: a first body 2710, a second body 2720, and a center body 2730. First body 2710 and second body 2720 are connected together (not shown) by a fastener, such as a screw/bolt.

As illustrated in FIG. 27B, first body 2710 in one embodiment has a cylindrical shape. Disposed through a center of first body 2710 is a center body conduit 2711. Disposed through first body 2710 are piston conduits 2712. There can be any number of piston conduits from 1 to a maximum number that can fit around first body 2710. As illustrated, there are three piston conduits 2712-1, 2712-2, and 2712-3. At the bottom 2714 of first body 2710 there can be o-ring seats 2714-1, 2714-2, and 2714-3 for piston conduits 2712-1, 2712-2, and 2712-3, respectively. Also, disposed through first body 2710 is a fluid conduit 2715.

As illustrated in FIGS. 27C to 27E, second body 2720 has a center body conduit 2721 that aligns with first body conduit 2711. Second body has piston conduits 2722 that match in number and alignment to the piston conduits 2712 of the first body. As shown, there are three piston conduits, 2722-1, 2722-2, and 2722-3. Piston conduits 2712-1, 2712-2, 2712-3, 2722-1, 2722-2, and 2722-3 all are disposed the same radial distance from the axial center 2701 of sample probe 2700.

There is a fluid channel 2723 disposed in the top 2724 of second body 2720. The fluid channel 2723 is in fluid communication with piston conduits 2722-1, 2722-2, and 2722-3. Fluid conduit 2715 terminates and is in fluid communication with fluid channel 2723. In one embodiment, there are an inner o-ring seat 2725 for accepting an o-ring and an outer o-ring seat 2726 for accepting an o-ring. The o-ring seats 2725 and 2726 provide a seal to fluid channel 2723.

As best seen in FIGS. 27D and 27E, piston conduits 2722-1, 2722-2, and 2722-3 have a first diameter 2727 that extends partially through second body 2720 and a second diameter 2728 that extends the remaining distance through second body 2720. The diameter of second diameter 2728 is approximately the same as the outer diameter of pistons 2705. The first diameter 2727 is greater than the second diameter 2728. Fluid from fluid channel 2723 is able to flow into first diameter 2727 of piston conduits 2722. Disposed coaxially along second diameter 2728 are one or more slots 2729. As shown, there are four slots 2729 in each piston channel 2722. The slots 2729 provide fluid communication from the first diameter 2727 through the second body 2720 such that a radius of first diameter 2727 and a radius of slot 2729. There can be an o-ring that sits in an o-ring seat 2709-2, 2709-3, and a third seat disposed around the outlets for piston conduits 2722-1, 2722-2, and 2722-3.

The center body 2730 is illustrated in FIGS. 27F to 27H. Center body 2730 has a shaft 2731 whose outside diameter is the same as the diameter of center body conduit 2711 and center body conduit 2712. Shaft 2731 is connected to a tip 2733. Tip 2733 is a cone whose base is the same diameter as first body 2710 and 2720 and tapers to a point. Piston conduits 2732-1, 2732-2, and 2732-3 are disposed through tip 2733. Disposed through shaft 2731 and into tip 2733 is sample fluid conduit 2736. Sample fluid conduit 2736 is in fluid communication with processing or testing systems. In the top 2737 of tip 2733 are fluid inlet ports 2734-1, 2734-2, and 2734-3, which are in fluid communication with fluid conduits 2735-2, 2735-3, and a third fluid conduit, respectively. The three fluid conduits are in fluid communication with sample fluid conduit 2736.

Pistons 2705-1, 2705-2, and a third piston are disposed through piston conduits 2712-1, 2712-2, 2712-3, 2722-1, 2722-2, 2722-3, 2732-1, 2732-2, and 2732-3, respectively, and they are driven by linear actuators, not shown, to raise and lower the pistons 2705-1, 2705-2, and the third piston. In one embodiment, the three pistons operate in unison. Center body 2730 is rotatable by a rotary actuator, not shown. The three pistons can have ends that are flat or pointed, or any shape that can assist in mixing. Also, the three pistons can be an ultrasonic horn to break up soil and assist in mixing.

In operation, center body 2730 is rotated so that piston conduits 2722-1, 2722-2, 2722-3 are aligned with piston conduits 2732-1, 2732-2, and 2732-3, respectively. Pistons 2705-1, 2705-2, and the third piston are retracted so that a desired void volume is formed in piston conduits 2722-1, 2722-2, 2722-3, 2732-1, 2732-2, and 2732-3, and optionally 2712-1, 2712-2, 2712-3. Alternatively, the three pistons can be fully extended to outlets of 2732-1, 2732-2, and 2732-3 first. Soil probe 2700 is plunged into soil (and pistons 2732-1, 2732-2, and 2732-3 are retracted if not already retracted), and soil fills piston conduits 2722-1, 2722-2, 2722-3, 2732-1, 2732-2, and 2732-3, and optionally 2712-1, 2712-2, 2712-3. At this point, pistons 2732-1, 2732-2, and 2732-3 are not in piston conduits 2732-1, 2732-2, and 2732-3. Center body 2730 is then rotated so that piston conduits 2722-1, 2722-2, 2722-3 are not in communication with piston conduits 2732-1, 2732-2, and 2732-3 and fluid inlet ports 2734-1, 2734-2, and 2734-3.

Pistons 2705-1, 2705-2, and the third piston are extended downward to compact the soil in piston conduits 2722-1, 2722-2, 2722-3. Center body 2730 is then rotated such that piston conduits 2722-1, 2722-2, 2722-3 and piston conduits 2732-1, 2732-2, and 2732-3 are aligned. Pistons 2705-1, 2705-2, and 2705-3 are actuated downward to a specified distance so that a known volume of soil in piston conduits 2722-1, 2722-2, 2722-3 is obtained. This expels any excess soil through piston conduits 2732-1, 2732-2, and 2732-3. Center body 2730 is then rotated to align piston conduits 2722-1, 2722-2, 2722-3 with fluid inlet ports 2734-1, 2734-2, and 2734-3, respectively. Fluid (such as extractant or other fluid, such as water) is injected through fluid conduit 2715 which communicates fluid to fluid channel 2723 which communicates fluid into piston conduits 2722-1, 2722-2, 2722-3 and slots 2729. Optionally, the three pistons can be oscillated up and down and/or rotated at any specified frequency to facilitate mixing of fluid with the soil. As the soil becomes fluidized, fluidized soil flows into fluid inlet ports 2734-1, 2734-2, and 2734-3 to fluid conduits 2735-2, 2735-3, and the third fluid conduit, respectively, and then into sample fluid conduit 2736. Fluid flow is stopped, and then center body 2730 is rotated to align piston conduits 2722-1, 2722-2, 2722-3 with piston conduits 2732-1, 2732-2, and 2732-3, and the pistons are extended to expel any remaining soil.

In an alternative embodiment, sample probe 2700 can be operated with the reverse flow of fluid. Fluid can flow from fluid conduit 2736 to fluid conduits 2735-2, 2735-3, and the third fluid conduit and then enter piston conduits 2722-1, 2722-2, and 2722-3 from the bottom and flow up to fluid channel 2723 and then to fluid conduit 2715. In this embodiment, slots 2729 act like a screen by only permitting soil that is sized to move through slots 2729. In this embodiment, oscillation of pistons 2705-1, 2705-2, and the third piston can draw fluid up to the top of soil and dissolve the soil in the fluid. This can minimize the amount of fluid needed to fluidize the soil.

2. Sample Processing Apparatus

A processing system 2820 can be a soil processing system or a vegetation processing system.

Figure 11A:
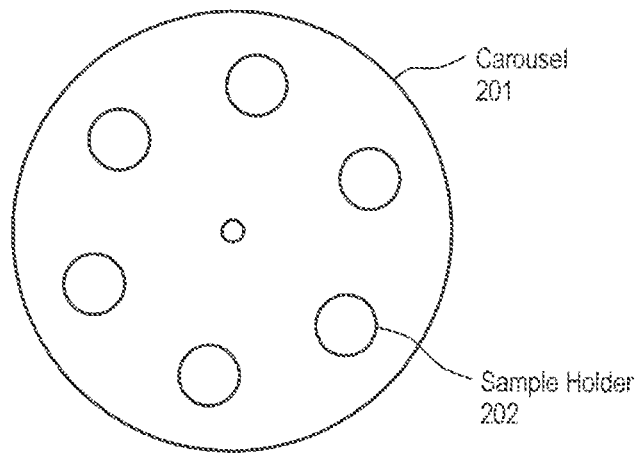
FIG. 11A illustrates a top elevation view of a carousel according to one embodiment.
Figure 11B:
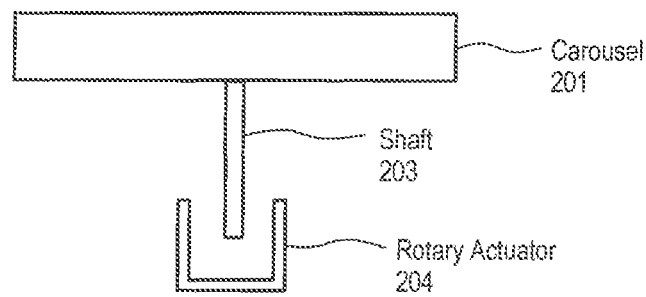
FIG. 11B illustrates a side elevation view of the carousel of FIG. 11A according to one embodiment.
Figure 11C:
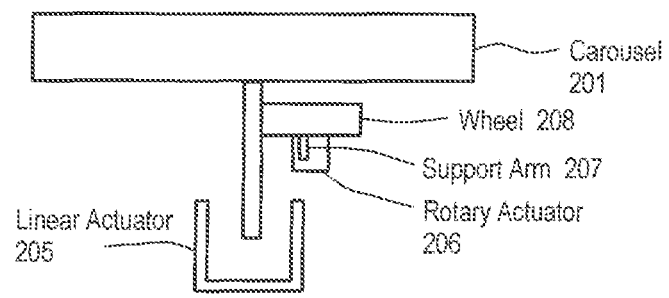
FIG. 11C illustrates a side elevation view of the carousel of FIG. 11A according to one embodiment.

FIG. 11A illustrates a top elevation view of a carousel according to one embodiment. FIG. 11B illustrates a side elevation view of the carousel of FIG. 11A according to one embodiment. FIG. 11C illustrates a side elevation view of the carousel of FIG. 11A according to one embodiment. To accommodate multiple samples during collection, during processing, or during testing, samples can be conveyed by sample conveyors. In one embodiment as shown in FIG. 11, a carousel 201 has multiple sample holders 202 for holding collection containers 121 or test containers (not shown). Carousel 201 is rotatable by having a rotary actuator 204 turning shaft 203, which is connected to carousel 201. Rotary actuator 204 is in communication with CPU 2820 for receiving signals to rotate carousel 201. In another embodiment, shaft 203 is actuated by linear actuator 205, which is in communication with CPU 2820, to raise or lower carousel 201 to deliver or remove a sample from a location. To rotate carousel 201, a wheel 208 is in contact with shaft 203. Wheel 208 is driven by rotary actuator 206, which is in communication with CPU 2820.

Figure 12A:
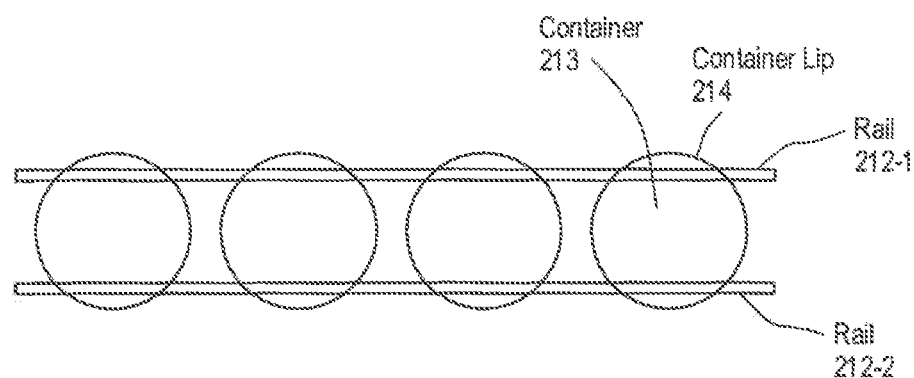
FIG. 12A illustrates a top elevation view of a conveyor system according to one embodiment.
Figure 12B:
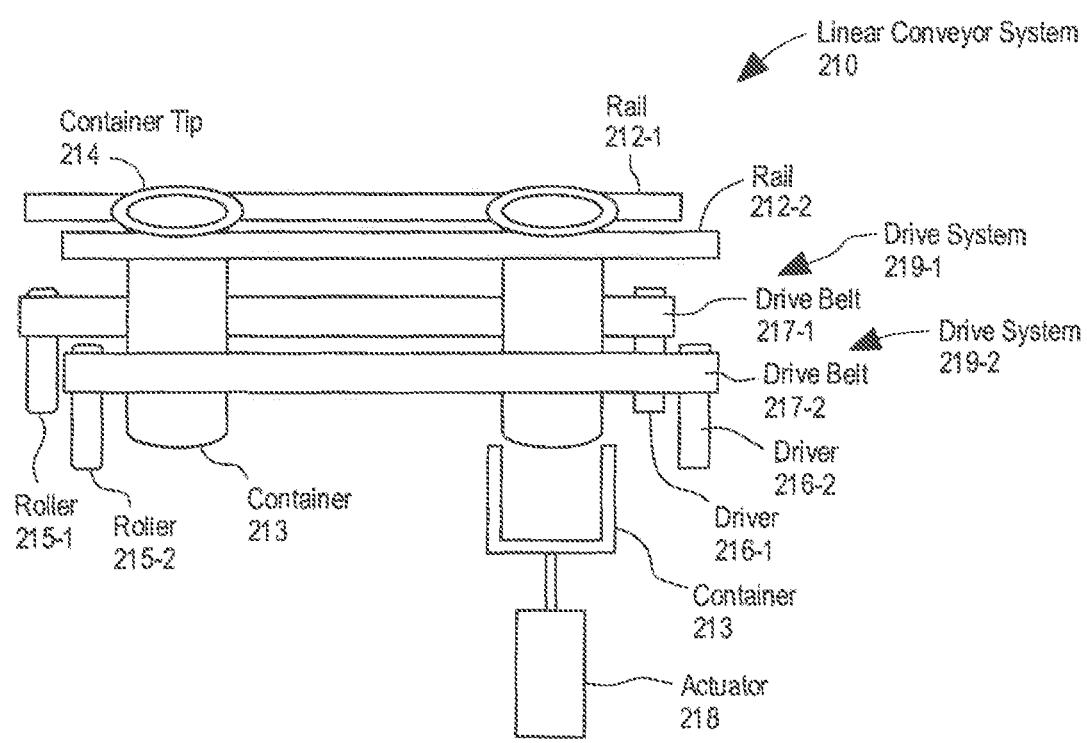
FIG. 12B illustrates a side elevation view of the conveyor system of FIG. 12A according to one embodiment.

FIG. 12A illustrates a top elevation view of a conveyor system according to one embodiment. FIG. 12B illustrates a side elevation view of the conveyor system of FIG. 12A according to one embodiment.

In another embodiment as shown in FIGS. 12A to 12B, a linear conveyor system 210 moves containers 213 (either collection containers 121 or test containers). Containers 213 have a lip 214. Container 213 is positioned between rails 212-1 and 212-2, and container lip 214 rests on rails 212-1 and 212-2. Positioned under rails 212-1 and 212-2 on each side of container 213 are drive systems 219-1 and 219-2. Each drive system 219-1 and 219-2 has a drive belt 217-1 or 217-2, respectively, disposed over drivers 216-1 and 216-2, respectively, and roller 215-1 and 215-2 respectively. Drive belts 217-1 and 217-2 frictionally engage containers 213. Drivers 216-1 and 216-2 are in communication with CPU 2820 to receive signals to move containers 213 along linear conveyor system 210. Containers 213 can be positioned in linear conveyor system 210 such that each container 213 is at a separate location for processing or testing. Optionally, container 213 can be positioned over an actuator 218, which is in communication with CPU 2820. Actuator 218 can either be linear (to raise or lower container 213) or rotary (to spin container 213).

Soil samples can be processed before testing to provide a more refined sample without aggregates and smaller particles for increased surface area. To remove aggregates, such as rocks, stones, or pebbles, soil samples can be strained through a screen. Examples of a screen include, but are not limited to, a screen with auger, soil trammel, roto-screen, push screen, and shake screen.

Figure 13A:
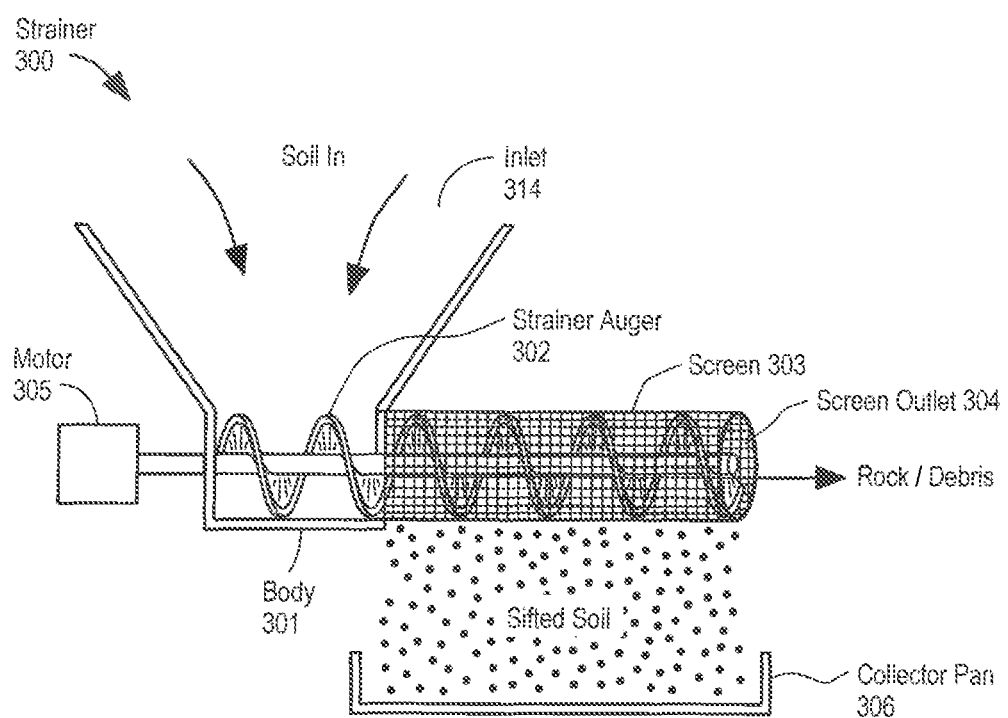
FIG. 13A illustrates a side elevation view of a strainer according to one embodiment.
Figure 13B:
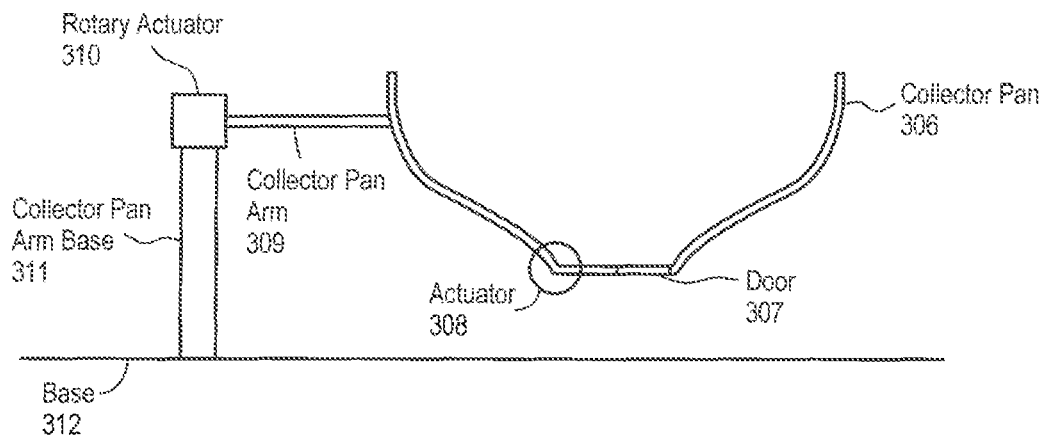
FIG. 13B illustrates a side elevation view of the collection pan of FIG. 13A according to one embodiment.
Figure 13C:
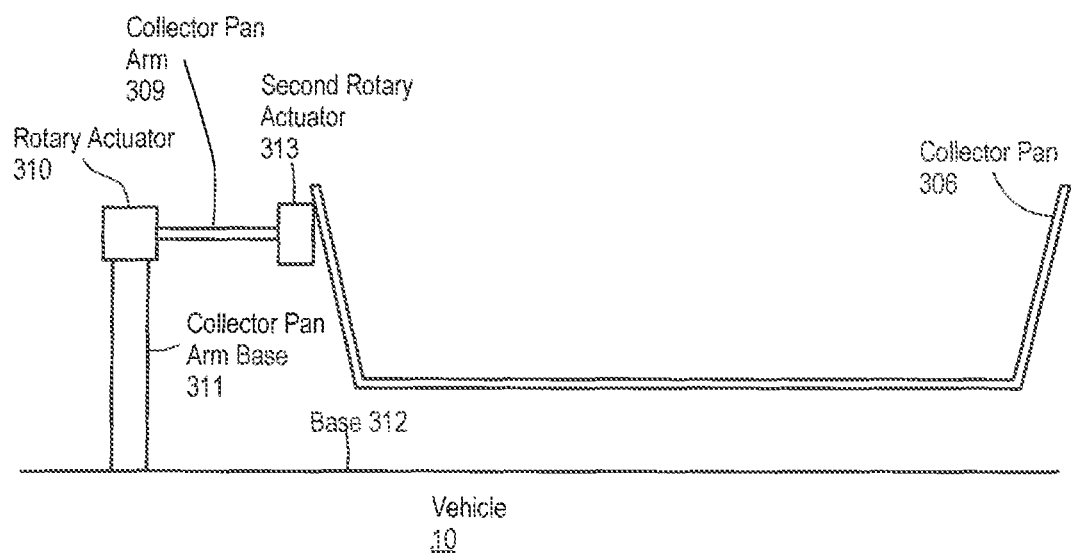
FIG. 13C illustrates a side elevation view of the collection pan of FIG. 13A according to one embodiment.

FIG. 13A illustrates a side elevation view of a strainer according to one embodiment. FIG. 13B illustrates a side elevation view of the collection pan of FIG. 13A according to one embodiment. FIG. 13C illustrates a side elevation view of the collection pan of FIG. 13A according to one embodiment.

As shown in FIG. 13A, soil can be separated from larger debris, such as rocks, through a strainer 300. Strainer 300 has in inlet 314 into body 301. A strainer auger 302 is disposed within the strainer body 301 and extends into screen 303, which is attached to strainer body 301. A motor 305 is connected to strainer auger 302 for driving strainer auger 302, and motor 305 is in communication with CPU 2820. Screen 303 can be a cylinder, or it can be tapered. Screen 303 has a screen outlet 304 opposite to where screen 303 attaches to strainer body 301. Screen outlet 304 allows rocks and other debris to exit the strainer 303. Screen 303 can have any desired mesh size. Sifted soil exits through screen 303. The sifted soil can be collected in collection pan 306.

From collection pan 306, as illustrated in FIG. 13C, the sample can be transferred directly to testing, or the sample can be further processed. A collection pan arm base 311 is attached to a base 312, which can be vehicle 10, and has a rotary actuator 310 at the end opposite to the end attached to base 312. A collection pan arm 309 is attached to the rotary actuator 310 and extends to a second rotary actuator 313, which is then connected to collection pan 306. Rotary actuator 310 and second rotary actuator 313 are in communication with CPU 2820, which can send signals to move collection pan 306 and then pour out collection pan 306 via the second rotary actuator 313.

In another embodiment shown in FIG. 13B, the second rotary actuator 313 can be removed, and the collection pan 306 can be connected to the collection pan arm. The collection pan 306 can have a door 307 with actuator 308 that is in communication with CPU 2820 for opening and closing the door 308. To remove the sample, door 307 can be opened to allow the sample to fall under gravity. The sample can be further processed as described below or tested directly.

Figure 14:
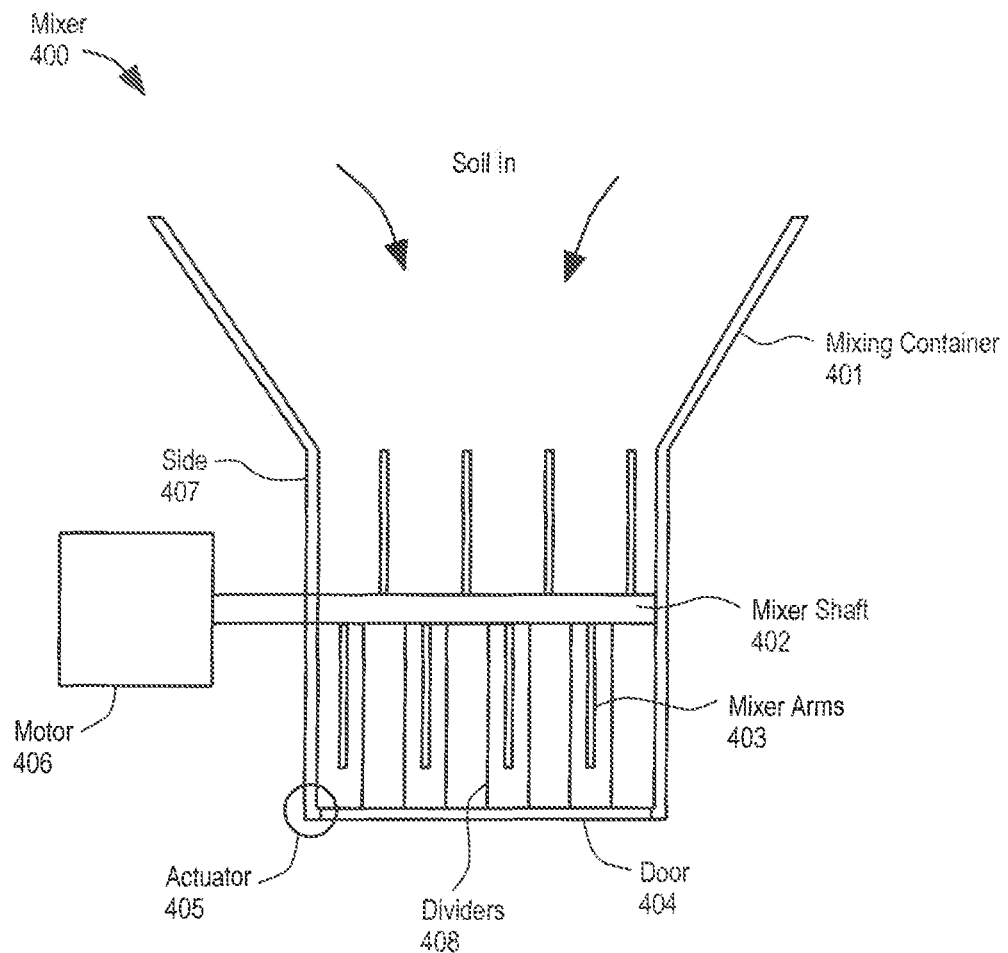
FIG. 14 illustrates a side sectional view of a mixer according to one embodiment.

FIG. 14 illustrates a side sectional view of a mixer according to one embodiment.

In one embodiment shown in FIG. 14, multiple samples can be mixed together or individual samples may be homogenized. Mixer 400 has a mixing container 401 and a mixer shaft 402 with mixing arms 403 disposed through a side 407 of mixer 400. Mixer shaft 402 is driven by a motor 406, which is in communication with CPU 2820. Optionally, mixing container 401 can have dividers 408 disposed in mixing container 401 attached to walls within mixing container 401 and spaced to be between mixer arms 403. Mixer shaft 402 is rotated to mix the sample (or samples) to achieve desired mixing. When mixing is complete, mixer 400 has a door 404 with actuator 405 that is in communication with CPU 2820 for opening and closing the door 404. To remove the sample, door 404 can be opened to allow the sample to fall under gravity.

Figure 15A:
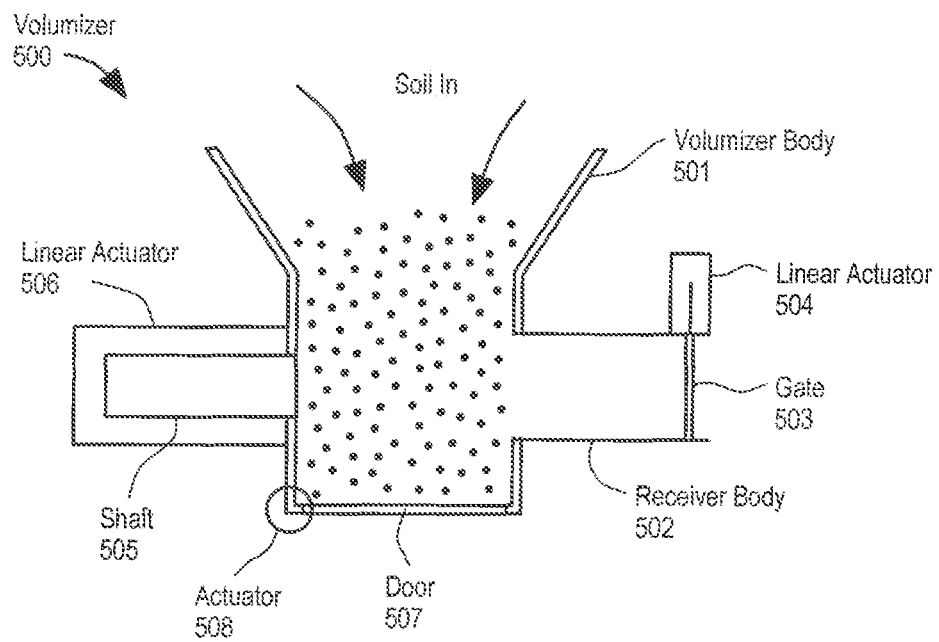
FIG. 15A illustrates a side section view of a volumizer according to one embodiment.
Figure 15B:
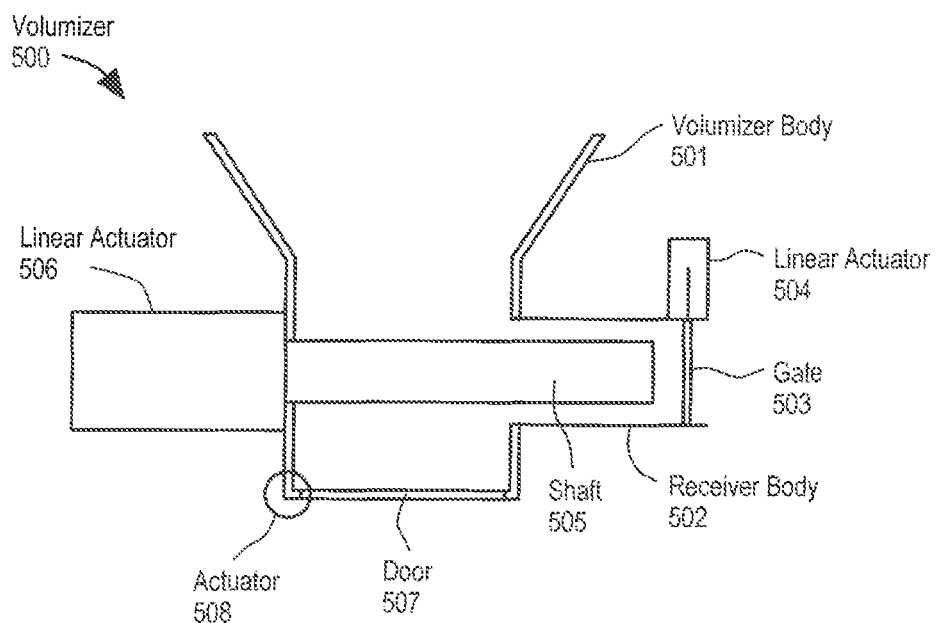
FIG. 15B illustrates a side section view of the volumizer of FIG. 15A with the shaft actuated.

FIG. 15A illustrates a side section view of a volumizer according to one embodiment. FIG. 15B illustrates a side section view of the volumizer of FIG. 15A with the shaft actuated.

In addition to or instead of mixing, samples can be volumized. As shown in FIGS. 15A and 15B, volumizer 500 has a volumizer body 501. Disposed through volumizer body 501 is a shaft 505, which is driven by linear actuator 506, which is in communication with CPU 2820. Opposite to where shaft 505 enters volumizer body 501 is a receiver body 502. When a select amount of soil has been collected, CPU 2820 sends a signal to linear actuator 504 to extend shaft 505 to force soil into receiver body 502 to a gate 503. Gate 503 is disposed at the end of receiver body 502 and is driven by a linear actuator 504, which is in communication with CPU 2820. Shaft 505 is extended until a specified force is obtained on the sample. This will indicate that the sample has achieved a specified density. Once the sample has a specified density, then a known volume of sample is obtained. CPU 2820 sends a signal to linear actuator 504 to open gate 503, and CPU 2820 sends a signal to extend shaft 505 a set distance to expel the sample of a known volume, and linear actuator 504 is then activated to close gate 503. After the sample is obtained, gate 503 is opened, and linear actuator 506 is activated to drive shaft 505 to expel the remaining material in the receiver body 502. Alternatively, gate 503 can be opened and shaft 505 extended to a point that leaves a known volume in the receiver body 502 and gate 503 is closed. This expelled sample is waste. Gate 503 is then opened and shaft 505 is extended fully to eject the sample of known volume. Volumizer body 501 further has a door 507 with actuator 508 that is in communication with CPU 2820 for opening and closing the door 507. To remove the excess sample, door 507 can be opened to allow the excess sample to fall under gravity.

Figure 20A:
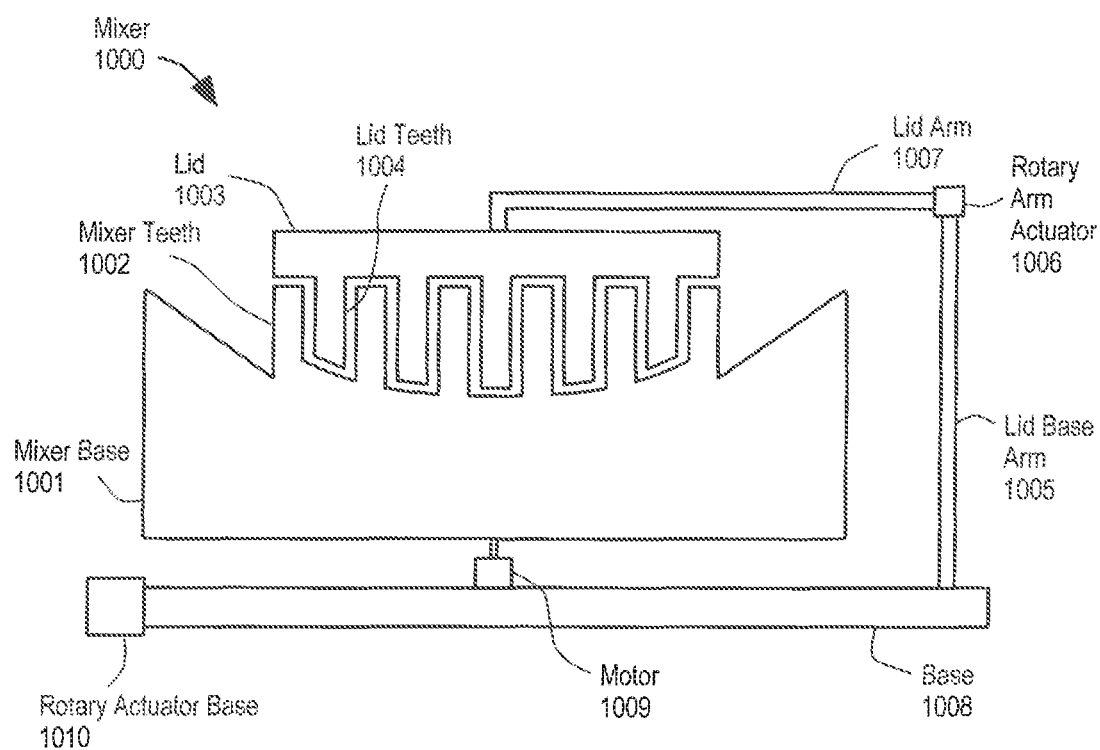
FIG. 20A illustrates a side sectional view of a mixer according to one embodiment.
Figure 20B:
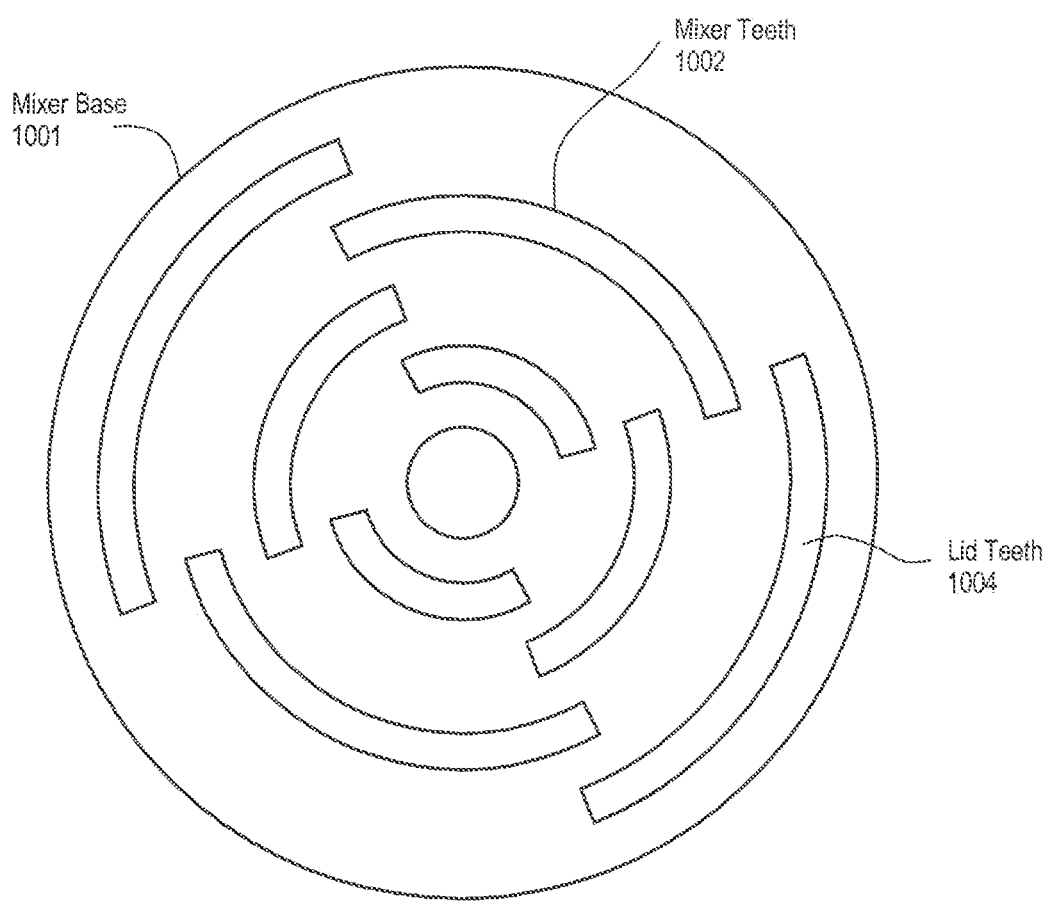
FIG. 20B illustrates a top view of the mixer of FIG. 20A.

FIG. 20A illustrates a side sectional view of a mixer according to one embodiment. FIG. 20B illustrates a top view of the mixer of FIG. 20A.

In another embodiment as illustrated in FIGS. 20A and 20B, another mixer 1000 is described. Mixer 1000 has a mixer base 1001 that is disposed on motor 1009 for spinning mixer base 1001. Motor 1009 is disposed on base 1008, which is connected to rotary actuator 1010 for rotating the base 1008 to empty the contents of mixer base 1001. Motor 1009 is in communication with CPU 2820 to actuate mixer base 1001. Extending above mixer base 1001 are mixer teeth 1002, which are curved about radii of mixer based 1001. A lid 1003 is disposed over mixer base 1001, and lid 1003 has lid teeth 1004 that are curved about radii of lid 1003. The mixer teeth and lid teeth are interposed with one another when lid 1003 is disposed on mixer base 1001. To raise and lower lid 1003 to permit samples to be added and removed, lid 1003 is connected to a lid arm 1007, which is connected to rotary actuator 1006, which is connected to lid base arm 1005, which is connected to base 1008. Actuator 1006 is in communication with CPU 2820 to raise or lower lid 1003.

Figure 16:
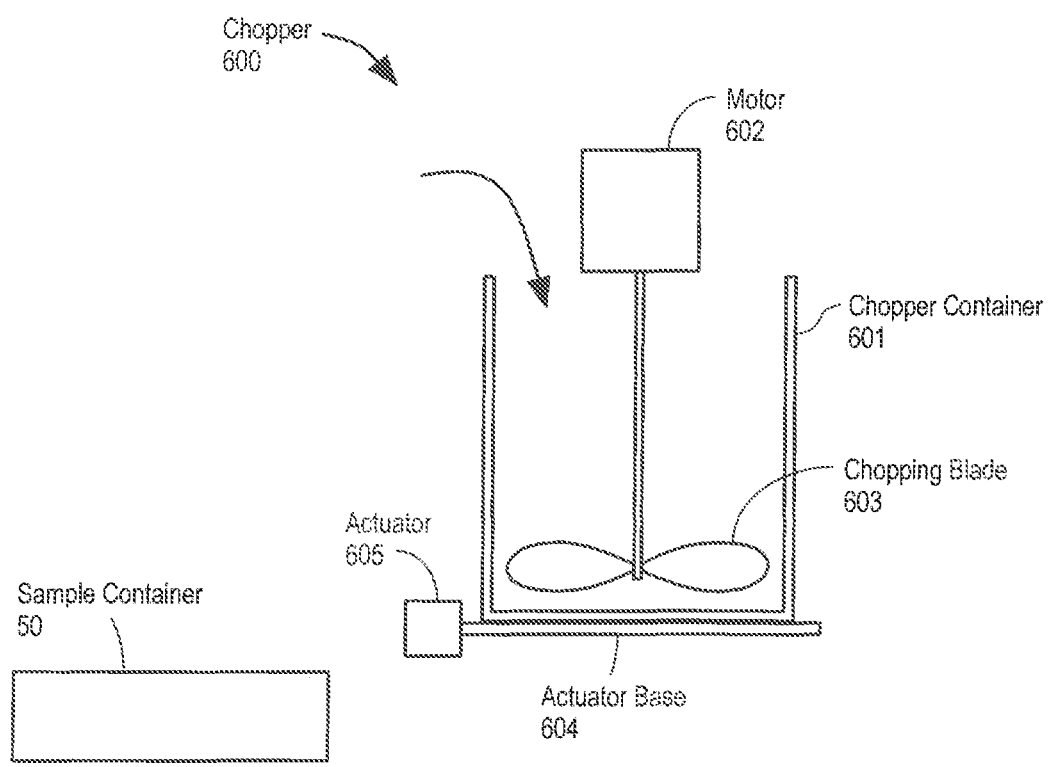
FIG. 16 illustrates a side elevation view of a chopper according to one embodiment.

FIG. 16 illustrates a side elevation view of a chopper according to one embodiment.

Vegetation samples can be processed to make smaller pieces of vegetation. A chopper 600 as shown in FIG. 16 can chop vegetation. Chopper 600 has a chopper container 601 with a chopping blade 603 inserted into the chopping container 601. Chopping blade 603 is driven by motor 602, which is in communication with CPU 2820 for actuating the chopper 600. Chopper 600 is disposed on base 604, which is connected to actuator 605, which is in communication with CPU 2820. After the vegetation is chopped, actuator 605 receives a signal to rotate base 604 to empty the contents of chopper container 601 into sample container 50.

Figure 17:
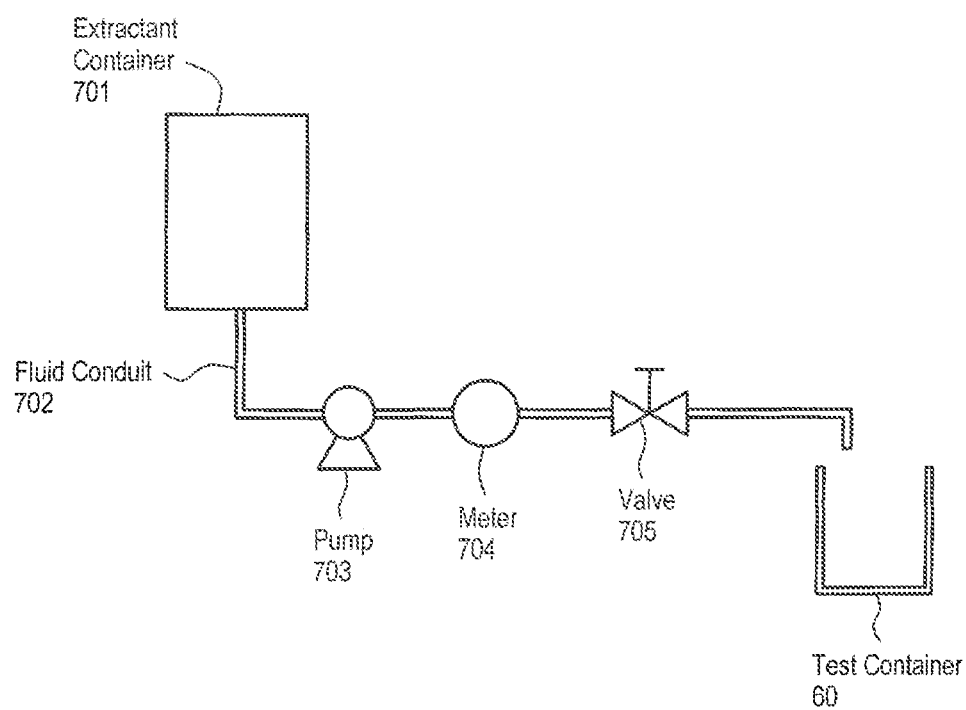
FIG. 17 illustrates a side elevation view of a flow system for extractant according to one embodiment.

FIG. 17 illustrates a side elevation view of a flow system for extractant according to one embodiment.

Once the soil and/or vegetation sample is taken, a test sample is prepared. An extractant and the sample are added to test container 60 and mixed with a mixer. The mixer is in communication with CPU 2820 to receive signals to mix. Alternatively, test container 60 can be a blender. The extractant is specifically chosen for extracting a chemical to be tested. In some embodiments, the extractant is water. In other embodiments, the extractant is any chemical extractant used to test for nutrients in soil and/or vegetation. Examples of extractants include, but are not limited to water, Mehlich 3 extractant, NaCl, DTPA (diethylenetriaminepentaacetic acid), AB-DTPA (ammonium bicarbonate-diethylenetriaminepentaacetic acid), Mehlich 1, Mehlich 2, Mehlich 3, $NH_4OAc$, Olsen P test extractant, Morgan extractant, Modified Morgan extractant, Bray-Kurtz extractant, $CaCl_2$, $BaCl_2$, $SrCl_2$, Hot Water, Truog extractant, Ambic extractant, $HNO_3$, LiCl, calcium-acetate-lactate, oxalate, citrate-bicarbonate-dithionite, HCl, acid ammonium oxalate.

In one embodiment illustrated in FIG. 17, the extractant is contained in extractant container 701. From extractant container 701, the extractant flows through fluid conduit 702 through pump 703, meter 704, and valve 705 to test container 60. Meter 704 is in signal communication with valve 705 and pump 703 through CPU 2820 to open and close the valve 705 to add a selected amount of extractant to the test container 60. The extractant and the sample amounts are measured to create the test sample with a known amount of sample per extractant to then provide a concentration of extracted chemical in the extractant.

Figure 18A:
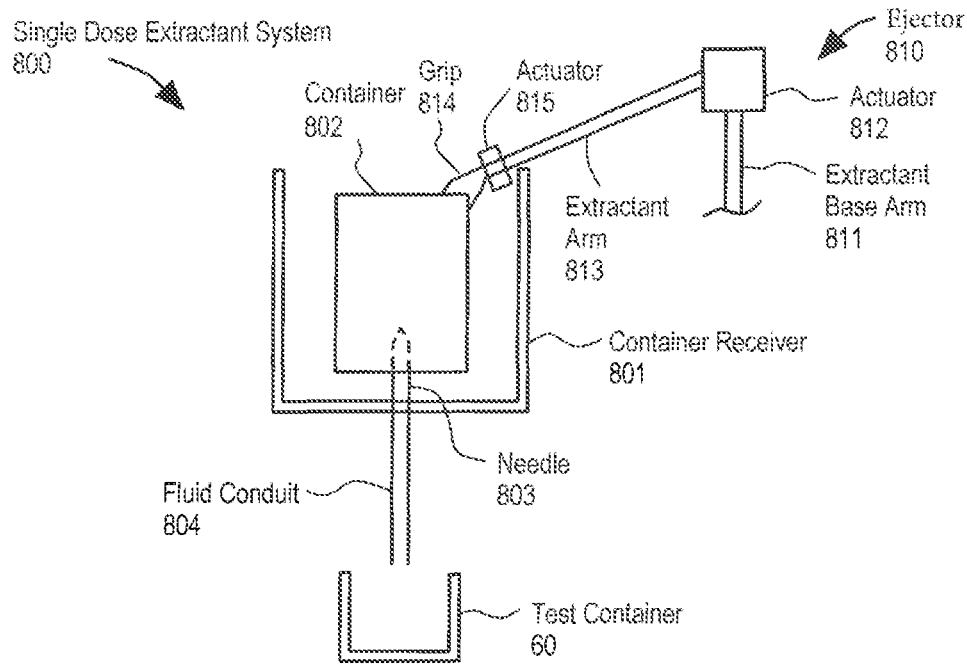
FIG. 18A illustrates a side elevation view of a single dose extractant system according to one embodiment.

FIG. 18A illustrates a side elevation view of a single dose extractant system according to one embodiment.

Figure 18B:
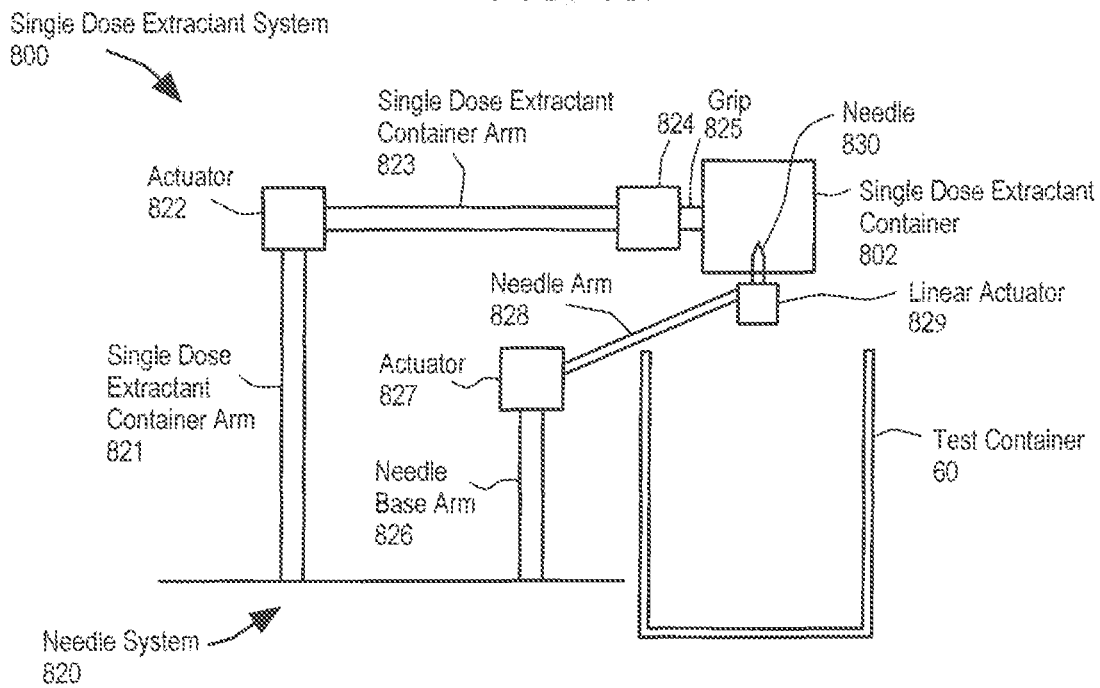
FIG. 18B illustrates a side elevation view of a single dose extractant system according to one embodiment.

FIG. 18B illustrates a side elevation view of a single dose extractant system according to one embodiment.

Figure 18C:
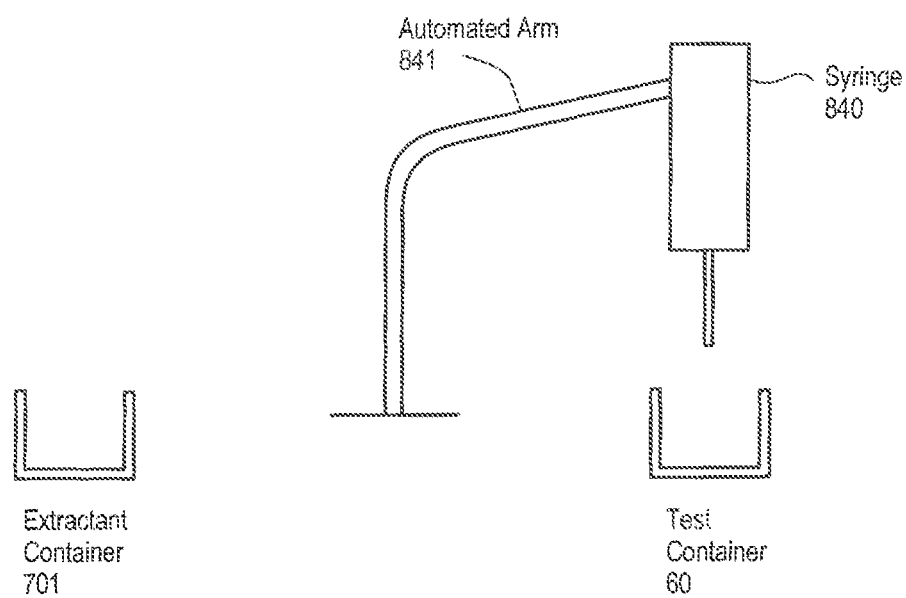
FIG. 18C illustrates a side elevation view of a syringe system according to one embodiment.

FIG. 18C illustrates a side elevation view of a syringe system according to one embodiment.

In another embodiment illustrated in FIG. 18A, extractant container 701 is a single dose extractant container 802. Single dose extractant container 802 is placed into container receiver 801 that has a needle 803 to puncture single dose extractant container 802 to allow the extractant to flow out of single dose extractant container 802 and into container receiver 801. Container receiver 801 can then be in place of extractant container 701 in the system described above. Alternatively, pump 703, meter 704, and valve 705 can be omitted with container receiver 801 flowing to test container 60. For extractants that are non-fluid, a solvent, such as water, can be injected into single dose extractant container 802 via injector that is in fluid communication with a solvent container (not shown). Container receiver 801 can contain a container ejector 810 to remove the single dose extractant container 802 so that a new single dose extractant container 802 can be used. Container ejector 810 is in communication with CPU 2820. Container ejector 810 has an ejector base arm 811 directly or indirectly connected to vehicle 10. An actuator 812 is disposed on ejector base arm 811 for moving ejector arm 813. Disposed on ejector arm 813 is an actuator 815 for actuating grip 814 for gripping and removing single dose extractant container 802. Each actuator 812 and 815 of container ejector 810 is in communication with CPU 2820. Upon ejection, the used single dose extractant container 802 can be collected for disposal. Container ejector 810 can also be commanded to grab and insert the single dose extractant container 802 into the container receiver 801.

In another embodiment shown in FIG. 18B, single dose container extractant container 802 is positioned over test container 60 by a single dose extractant system 800. Single dose extractant system 800 has a single dose extractant container base arm 821 directly or indirectly connected to vehicle 10. An actuator 822 is disposed on single dose extractant container base arm 821 for actuating a single dose extractant container arm 823. Disposed on single dose extractant container arm 823 is an actuator 824 actuating grip 825 for gripping single dose extractant container 802. Each actuator 822 and 824 are in communication with CPU 2820 for receiving signals to actuate. Single dose extractant system 800 takes a single dose extractant container 802 and moves it over the test container 60. A needle system 820 has a needle base arm 826 directly or indirectly connected to vehicle 10. An actuator 827 is disposed on needle base arm 826 to actuate needle arm 828. A linear actuator 829 is disposed on needle arm 827 to actuate a needle 830 to puncture single dose extractant container 802. Each actuator 827 and 829 are in communication with CPU 2820 for receiving signals to actuate.

The extractant can be ready to use such that no dilution of the extractant is needed. In another embodiment, the extractant can be stored on vehicle 10 as a concentrate that is then diluted to use concentration with water. In this embodiment, water would be added to sample container 50 as described above, and extractant is added to sample container with a similar fluid conduit 702, pump 703, meter 704, and valve 705. In another embodiment, the reagent can be a non-fluid. Examples of non-fluids include, but are not limited to, solids, powder, granules, pellets, dissolvable patch, pod (solid inside a dissolvable film).

Pump 703 can be any pump that is sized to deliver the needed amount of extractant. In certain embodiments, pump 703 is a peristaltic pump.

In another embodiment, fluid conduit 702, pump 703, meter 704, and valve 705 are replaced with a syringe 840. This can be used in the embodiment for delivering extractant to sample container 50 for dilution since syringe 840 can be sized to measure smaller quantities. In one embodiment, syringe 840 is a SGE™ eVol™ Handheld Automated Analytical Syringe from Fisher Scientific that is in data communication with CPU 2820. Syringe 840 is moved by automated arm 841 that is in data communication with CPU 2820. A signal is sent to automated arm 841 to move syringe 840 into contact with the extractant in extractant container 701. A signal is sent to syringe 840 to withdraw a specified amount of extractant. Automated arm 841 then receives a signal from CPU 2820 to move syringe 840 to test container 60, and then CPU 2820 sends a signal to syringe 840 to dispense the extractant into test container 60.

Multiple extractants can be used to test for different nutrients. In this embodiment, there is an extractant container 701, fluid conduit 702, meter 703, pump 704, and valve 705 for each extractant. In this embodiment, the amount of soil and/or vegetation collected at each point can be sized such that when divided there is enough sample for each test.

Figure 19A:
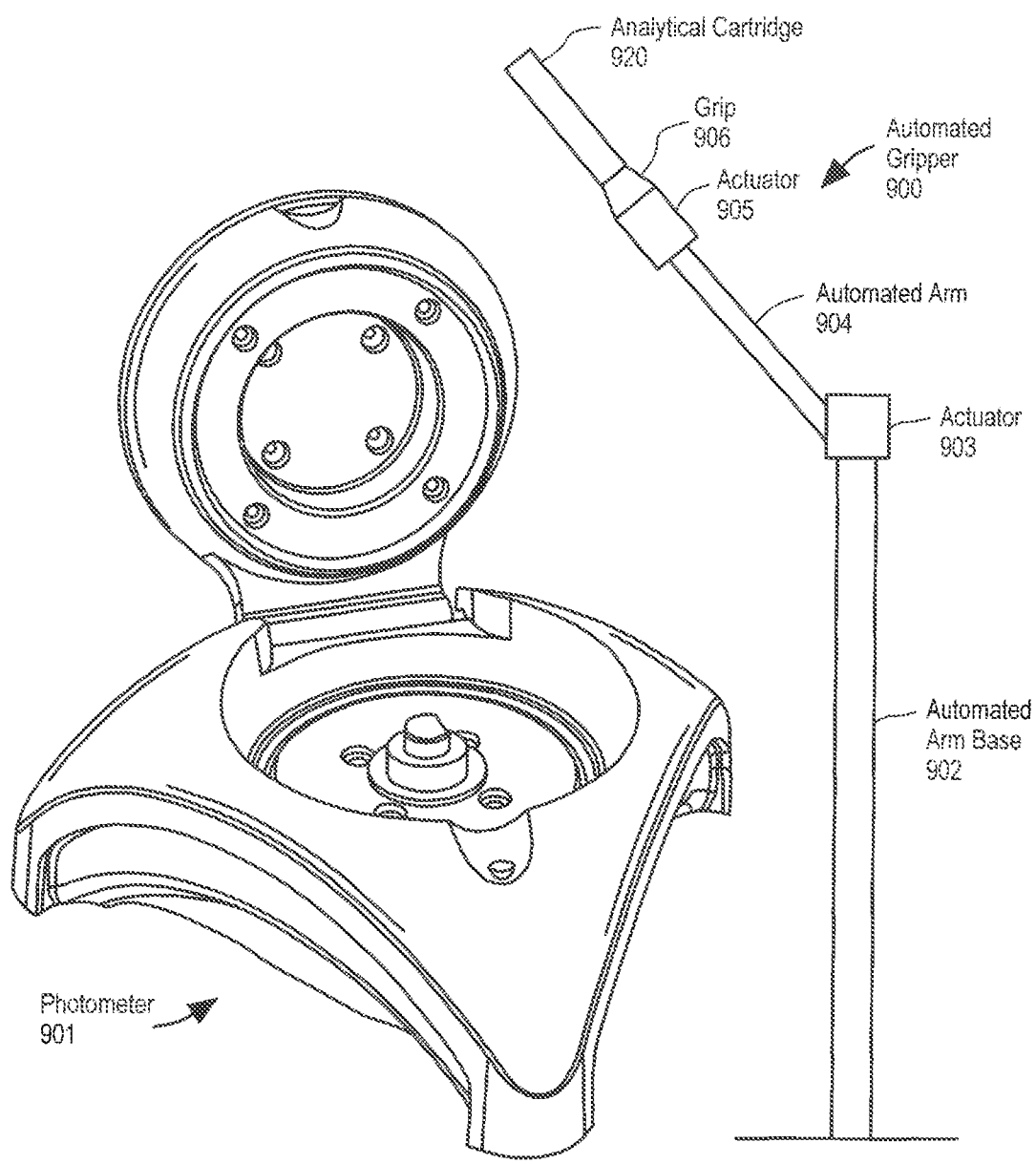
FIG. 19A illustrates a perspective view of a photometer and analytical cartridge system according to one embodiment.

FIG. 19A illustrates a perspective view of a photometer and analytical cartridge system according to one embodiment.

Figure 19B:
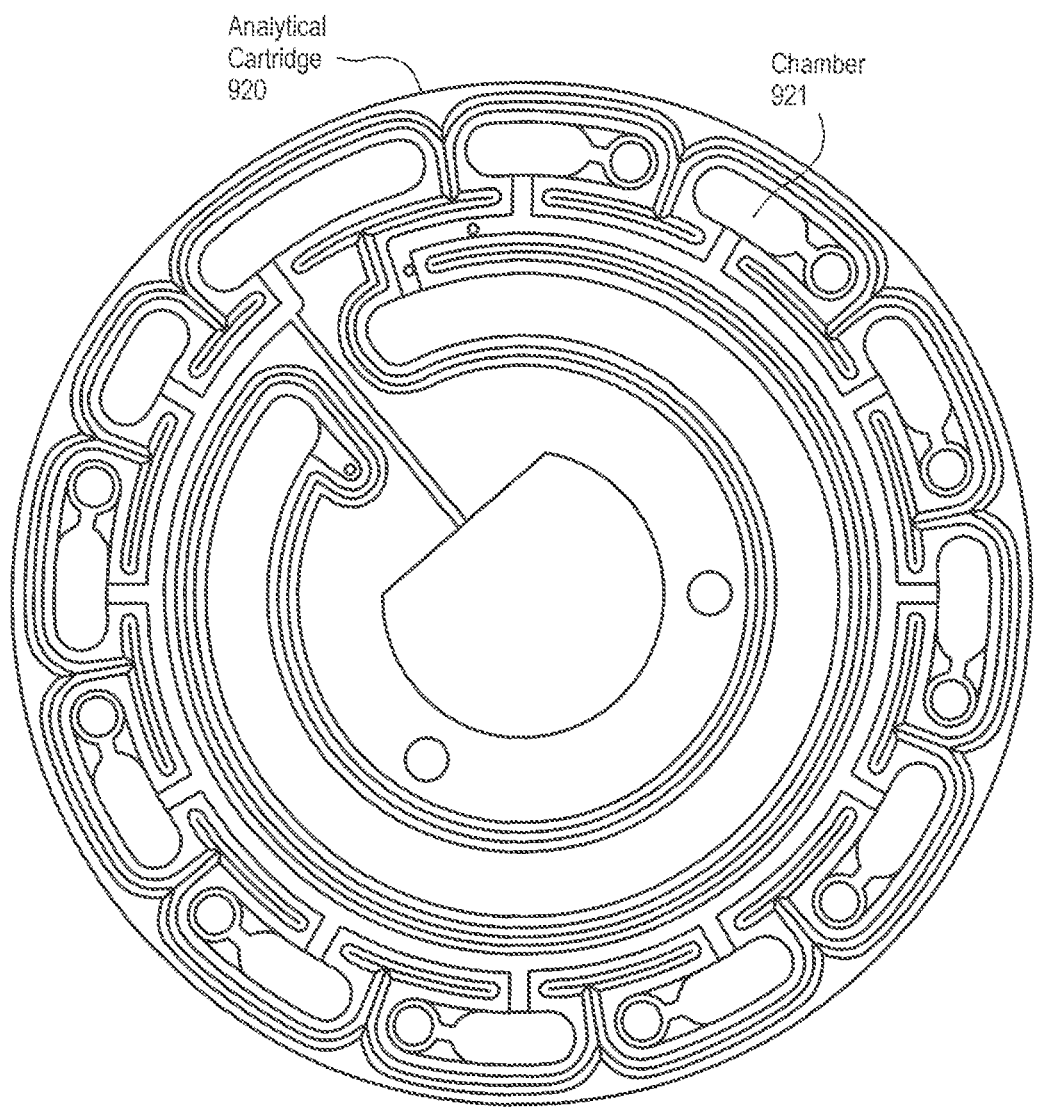
FIG. 19B illustrates a top elevation view of the analytical cartridge of FIG. 19A.

FIG. 19B illustrates a top elevation view of the analytical cartridge of FIG. 19A.

In another embodiment as illustrated in FIGS. 19A and 19B, one or more extractants can be in an analytical cartridge 920, such as described in U.S. Pat. No. 8,734,734. Each chamber 921 of analytical cartridge 920 can have a different extractant. For extractants that can mix easily, the magnetically moveable element may not be needed. A test sample is added to the analytical cartridge 920 and flows to each chamber 921 to mix with the extractant in each chamber 921. Analytical cartridge 920 is spun in a photometer 901, which is in communication with CPU 2820. First, automated gripper 900 receives a signal from CPU 2820 to take an analytical cartridge 920 and insert analytical cartridge 920 into photometer 901. Automated gripper 900 has an automated arm base 902 that is directly or indirectly connected to vehicle 10. An actuator 903 is connected to automated arm base to actuate an automated arm 904. Automated arm 904 has an actuator 905 to actuate grip 906 to grip analytical cartridge 920. Each actuator 903 and 905 are in communication with CPU 2820 to actuate.

In some embodiments, to add the test sample, a test syringe (which can be similar to syringe 840 above) is moved by automated gripper 900, which is in data communication with CPU 2820. Automated gripper 900 has an automated arm base 902, which is connected directly or indirectly to vehicle 10. An actuator 903 is disposed on automated arm base 902 for actuating automated arm 904. Disposed on automated arm 904 is an actuator 905 actuating grip 906 for gripping analytical cartridge 920. Each actuator 903 and 905 are in communication with CPU 2820 for receiving signals to actuate. A signal is sent to automated gripper 900 to move the test syringe into contact with test sample. A signal is sent to the test syringe to withdraw a specified amount of sample. Automated gripper 900 then receives a signal from CPU 2820 to move the test syringe to analytical cartridge 920, and then CPU 2820 sends a signal to the test syringe to dispense the sample into analytical cartridge 920. Photometer 901 receives a signal from CPU 2820 to spin analytical cartridge 920 and then measure color in each chamber 921 and communicate the results to CPU 2820. Automated gripper 900 can then receive a signal to move the used analytical cartridge 920 from photometer 901 for disposal.

FIG. 21 illustrates a side sectional view of a separator according to one embodiment.

In another embodiment as illustrated in FIG. 21, a separation system 1100 can be included after test sample is prepared above to separate the extracted fluid from the soil and/or vegetation. A separator 1101 has an inner bowl 1104 for receiving samples, and an outer collection space 1102 for collecting filtered samples. Disposed on a lip 1110 between inner bowl 1104 and outer collection space 1102 is a filter ring 1103. A lid 1105 is connected to lid arm 1107, which is connected to an actuator 1108, which is connected to a lid arm base 1134, which is connected directly or indirectly to the vehicle 10. Actuator 1108 is in communication with CPU 2820 to receive signals to raise or lower lid 1105 to engage or disengage from separator 1101. Lid side 1106 extends down to contact separator 1101 at an outer portion of outer collection space 1102 to provide a seal for outer collection space 1102. Separator 1101 has a shaft 1112 connected to its bottom, which is driven by motor 1111, which is in communication with CPU 2820 to receive signals to drive the separator 1101. Motor 1111 is connected to a base 1114, which is connected to a rotary actuator 1113, which is in communication with CPU 2820. A sample is placed in inner bowl 1104, lid 1105 is engaged with separator 1101, and then separator 1101 is spun. The spinning allows fluid to separate from the sample and flow through filter ring 1103 to the outer collection space 1102. Once separated, separator 1101 is stopped from spinning. Lid 1105 is retracted from separator 1101. The test syringe, described above, is inserted into the fluid in outer collection space 1102 to withdraw a test sample. Separator 1101 is then emptied of the sample by rotary actuator 1113 receiving a signal from CPU 2820 to rotate the base 1114 such that separator 1101 pours its contents into waste collection 1115. Alternatively, base 1114 and rotary actuator 1113 can be replaced with the rotary actuator 1207, arms 1205-1 and 1205-2 and pivot 1206 in FIG. 22 described below.

Test samples can be prepared based on a single sample, or multiple samples from multiple points in the field can be combined to provide an average across the multiple points.

Figure 22:
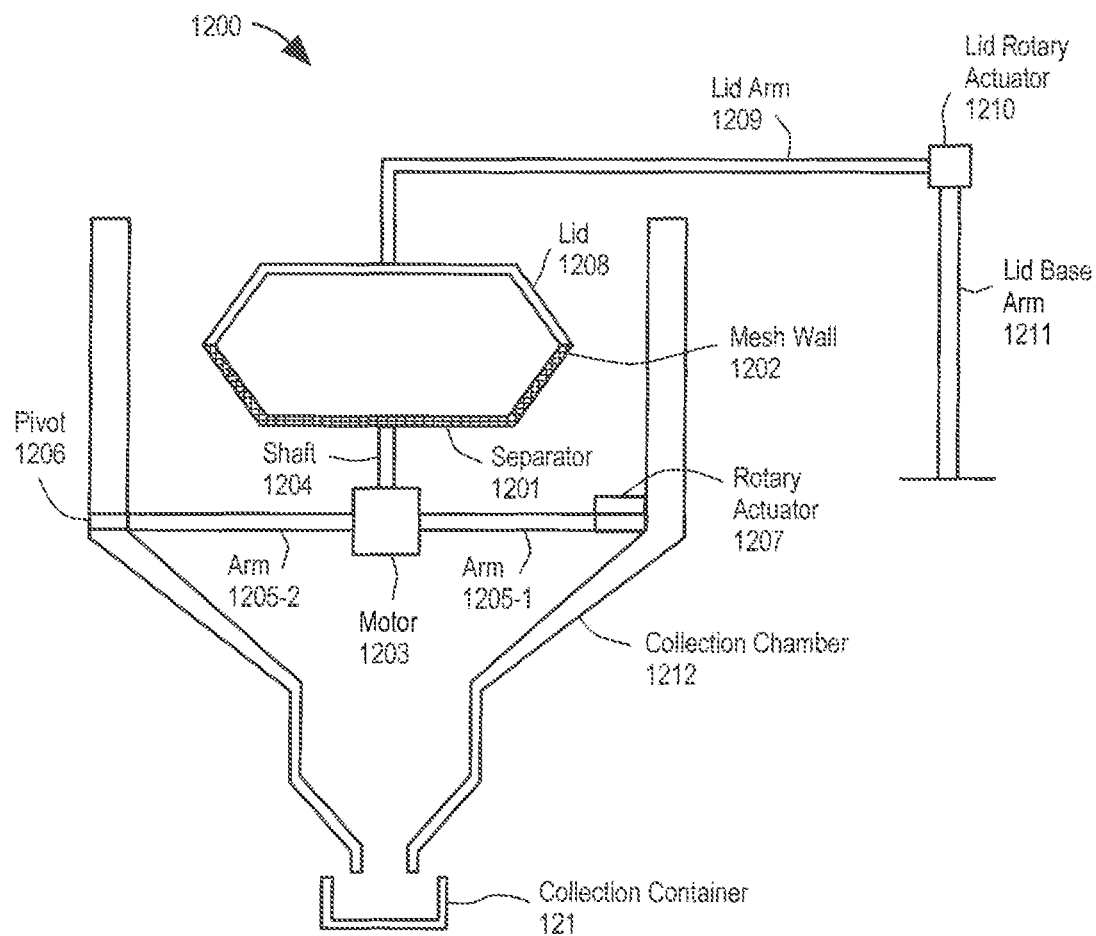
FIG. 22 illustrates a side sectional view of a separator according to one embodiment.

FIG. 22 illustrates a side sectional view of a separator according to one embodiment.

In another embodiment illustrated in FIG. 22, separator system 1200 is described. Separator system 1200 has a collection chamber 1212. Disposed across collection chamber 1212 is a rotary actuator 1207 connected to arm 1205-1, connected to motor 1203, connected to arm 1205-2, connected to pivot 1206. Actuator 1207 and motor 1203 are in communication with CPU 2820. Motor 1203 is connected to a shaft 1204, which is connected to separator 1201. Separator 1201 has a mesh wall 1202 for allowing fluid to flow through it while retaining solids. Engaging separator 1201 is lid 1208. Lid 1208 is connected to lid arm 1209, which is connected to rotary actuator 1210, which is connected to lid base arm 1211, which is directly or indirectly connected to vehicle 10. When a sample is added to separator 1201, CPU 2820 sends a signal to rotary actuator 1210 to close lid 1208. CPU 2820 then sends a signal to motor 1203 to spin separator 1201. Liquid is expelled through mesh wall 1202 into collection chamber 1212 and then drains into collection container 121. When separation is complete, motor 1203 is stopped, and lid 1208 is raised by actuating rotary actuator 1210. After collection container 121 is removed, rotary actuator 1207 is actuated to rotate separator to pour the contents into collection chamber 1212 to flow out the bottom of collection chamber 1212.

3. Sample Testing Apparatus

Figure 23A:
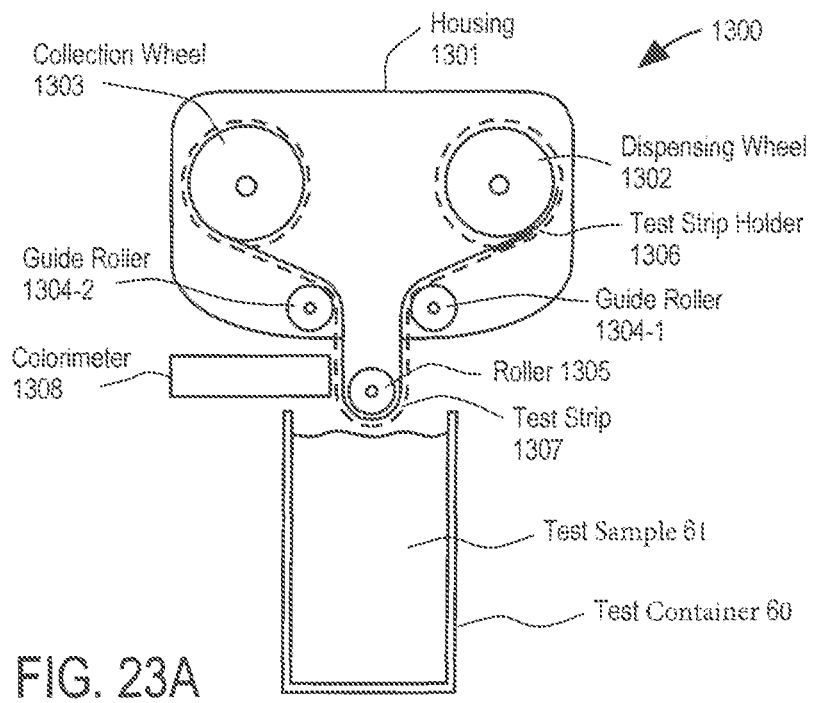
FIG. 23A illustrates a side sectional view of a test strip cassette according to one embodiment.

FIG. 23A illustrates a side sectional view of a test strip cassette according to one embodiment.

Figure 23B:
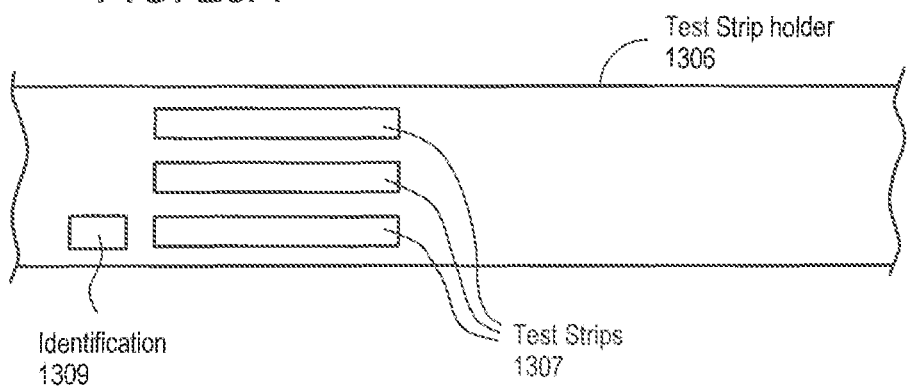
FIG. 23B illustrates a top elevation view of a test strip holder with test strips according to one embodiment.

FIG. 23B illustrates a top elevation view of a test strip holder with test strips according to one embodiment.

Figure 23C:
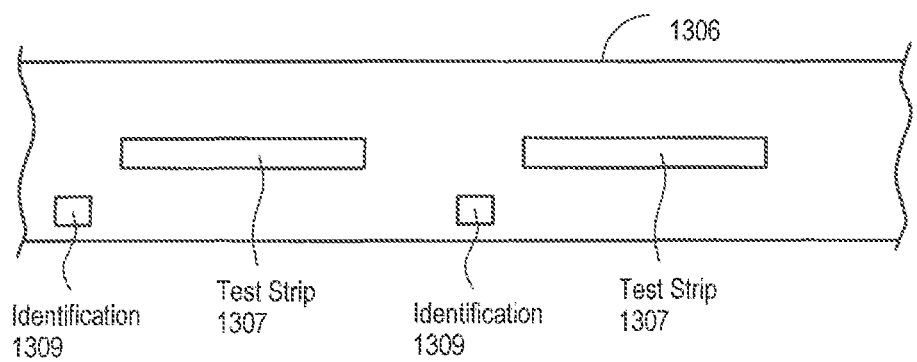
FIG. 23C illustrates a top elevation view of a test strip holder with test strips according to one embodiment.

FIG. 23C illustrates a top elevation view of a test strip holder with test strips according to one embodiment.

In one embodiment, a test strip apparatus 1300 is used to test a test sample 61. As illustrated in FIG. 23, test strip apparatus 1300 includes a test strip holder 1306 loaded onto dispensing wheel 1302 and wound around a roller 1305 to a collection wheel 1303. Roller 1305 allows for test strip holder 1306 to be positioned to allow for the test strip holder 1306 to be placed in test sample 61. Optionally, guide rollers 1304-1, 1304-2 can be included to further guide test strip holder 1306. A motor (not shown) drives collection wheel 1303 to pull test strip holder from dispensing wheel 1302. The motor can be an electrical motor or an electromechanical motor, and it is in data communication with CPU 2820 for controlling the advancement of test strip holder 1306 to the next available test strip 1307 for testing samples.

In some embodiments, on test strip holder 1306 are test strips 1307 that are chemically reactive to selected chemicals and change color based on the chemical concentration in the test solution. Each test strip 1307 has an identification 1309 that is associated with a geo-referenced location of a test sample 61 that is tested by test strip 1307. When multiple test strips 1307 are used to test sample 61 (such as with different chemicals), test strips 1307 can share the same identification 1309 or each can have its own identification 1309. Test strip holder 1306 can hold multiple types of test strips 1307 for testing different chemicals. Test strips 1307 for different chemicals can be disposed side by side of each other on test strip holder 1306, or they can be disposed sequentially along test strip holder 1306.

In one embodiment, a colorimeter 1308 can be included to read the color of each test strip 1307 after it leaves test sample 61 and before winding onto collection wheel 1303, which is enclosed within housing 1301. Colorimeter 1308 can then be in data communication with memory storage 2805 and CPU 2820. Alternatively, test strip holder 1306 can be collected and tested after all sampling is completed. In any of these embodiments, a data map can be generated that associates test results for each chemical tested at each location in the field. The identification can be any identification that uniquely identifies the sample tested. The identification includes, but is not limited to, an alpha indicium, a numeric indicium, an alphanumeric indicium, a bar code, or a QR code.

In other embodiments, test strip apparatus 1300 and colorimeter 1308 are replaced by one or more ion-selective electrodes (not shown) that are immersed in test sample 61. Ion-selective electrodes are in data communication with CPU 2820 and memory 2805 to record the results for each sample tested. In other embodiments, a spectrophotometer (not shown) is used to analyze the samples. The spectrophotometer is in data communication with CPU 2820 and memory 2805.

If not already set to have an untested test strip 1307, collection wheel 1303 is advanced to have an untested test strip 1304 positioned at roller 1305. Test strip apparatus 1300 can be lowered to submerge test strip 1307 at roller 1305 into sample container 50, or sample container 50 can be raised to submerge test strip 1307. Test strip 1307 remains submerged in test sample 61 in sample container 50 for a specified amount of time for test strip 1307 to react with the test sample 61. The amount of time varies based on the type of chemical tested. After the amount of time has been reached, test strip 1307 is removed from test sample 61 by either raising test strip apparatus 1300 or lowering sample container 50. Test sample 61 is then disposed of. If the extractant is water, test sample 61 can be drained to the ground, or test sample 61 can be transferred to a disposal container (not shown) for later disposal. Sample container 50 is then rinsed with water and is ready for another sample.

Figure 24A:
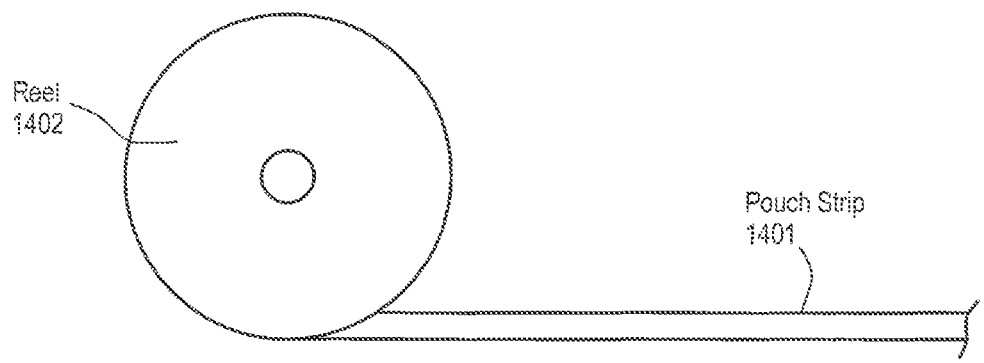
FIG. 24A illustrates a side elevation view of a pouch strip according to one embodiment.

FIG. 24A illustrates a side elevation view of a pouch strip according to one embodiment.

Figure 24B:
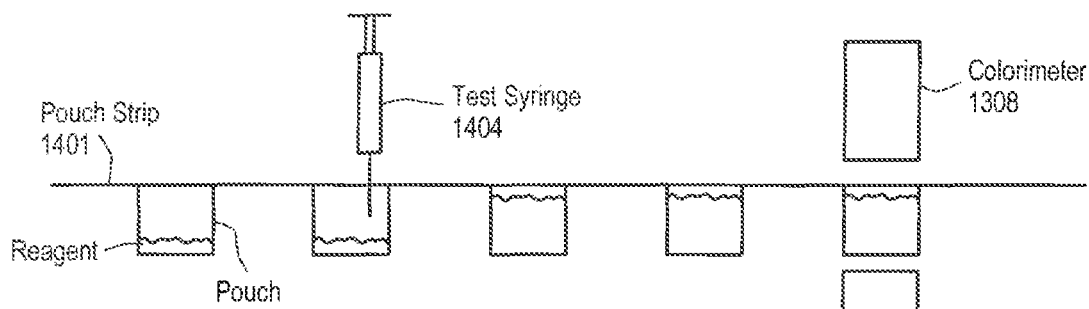
FIG. 24B illustrates a top elevation view of the pouch strip of FIG. 24A according to one embodiment.

FIG. 24B illustrates a top elevation view of the pouch strip of FIG. 24A according to one embodiment.

Figures 24C, 24D:
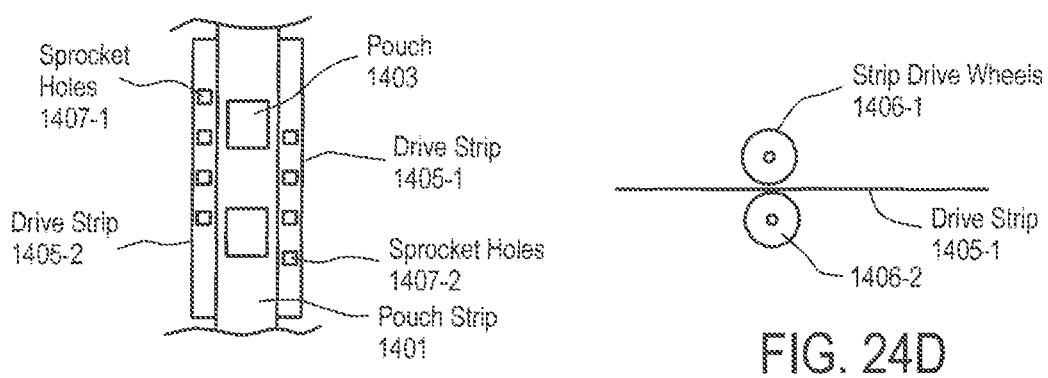
FIG. 24C illustrates a top elevation view of the pouch strip of FIG. 24A and drive strips according to one embodiment.
FIG. 24D illustrates a side elevation view of drive wheels for the pouch strip of FIG. 24A.

FIG. 24C illustrates a top elevation view of the pouch strip of FIG. 24A and drive strips according to one embodiment.

FIG. 24D illustrates a side elevation view of drive wheels for the pouch strip of FIG. 24A.

Figure 24E:
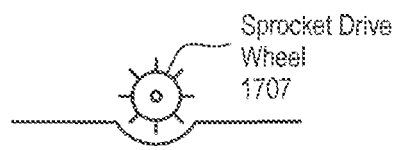
FIG. 24E illustrates a side elevation view of a sprocket drive wheel 1707 for the pouch strip of FIG. 24B.

FIG. 24E illustrates a side elevation view of a sprocket drive wheel 1707 for the pouch strip of FIG. 24B.

In another embodiment as shown in FIGS. 24A to 24E, a reel 1402 has a pouch strip 1401 wound onto reel 1402. Pouch strip 1401 has pouches 1403 disposed within it. Each pouch 1403 has a reagent stored within the pouch 1403. On each side of pouch strip 1403, there are drive strips 1405-1 and 1405-2. In one embodiment, each drive strip 1405-1 and 1405-2 can be driven by strip drive wheels 1406-1 and 1406-2 by friction. In another embodiment, at least one drive strip 1405-1 and 1405-2 contains sprocket holes 1407-1 and 1407-2 to be driven by at least one sprocket drive wheel 1707 as illustrated in FIG. 24E.

To add test sample 61, test syringe 1404 (which can be similar to syringe 840 above) is moved by a similar system that moves syringe 840.

4. Vehicle

Figure 26:
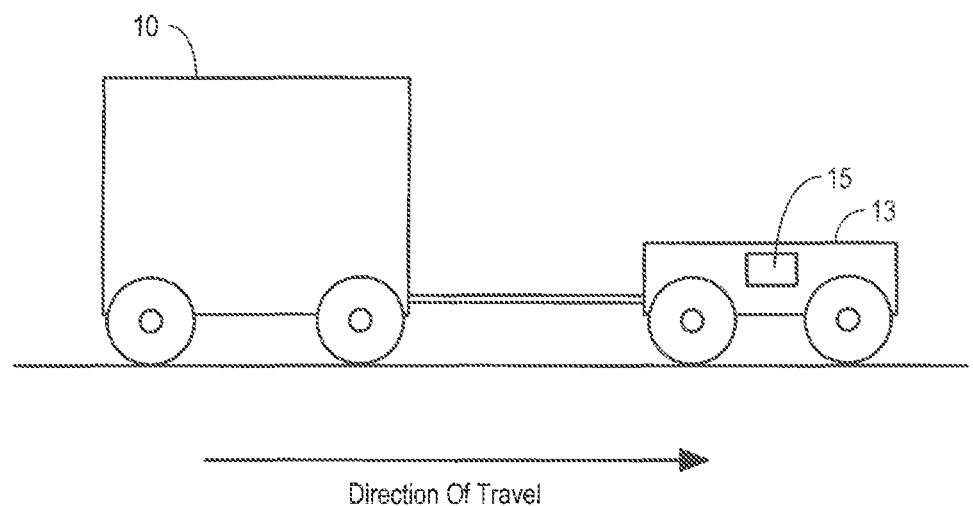
FIG. 26 illustrates a side elevation view of a vehicle with a cart disposed ahead of the vehicle with collection, processing, and testing according to one embodiment.

FIG. 26 illustrates a side elevation view of a vehicle with a cart disposed ahead of the vehicle with collection, processing, and testing according to one embodiment.

In one embodiment, the collection system 15 can be disposed on the front of vehicle 10 in a direction of travel (not shown) or ahead of vehicle 10 in a direction of travel on a cart 13 as illustrated in FIG. 26. Cart 13 can also have any of the above described equipment to process and/or test samples. Having the collection system 15 ahead of vehicle 10 allows for testing of soil and/or vegetation to provide data about the tested property to then change an agricultural operation on the vehicle 10. For example, an amount of a nutrient being applied to the field by vehicle 10 can be varied based on an amount needed for the specific location. In this embodiment, it is not necessary to associate the test strip 1307 with the identification 1309 since the test results are immediately used to change the agricultural operation. While not required, it is preferable to include the identification 1309 to so that a map can be created.

Figure 25:
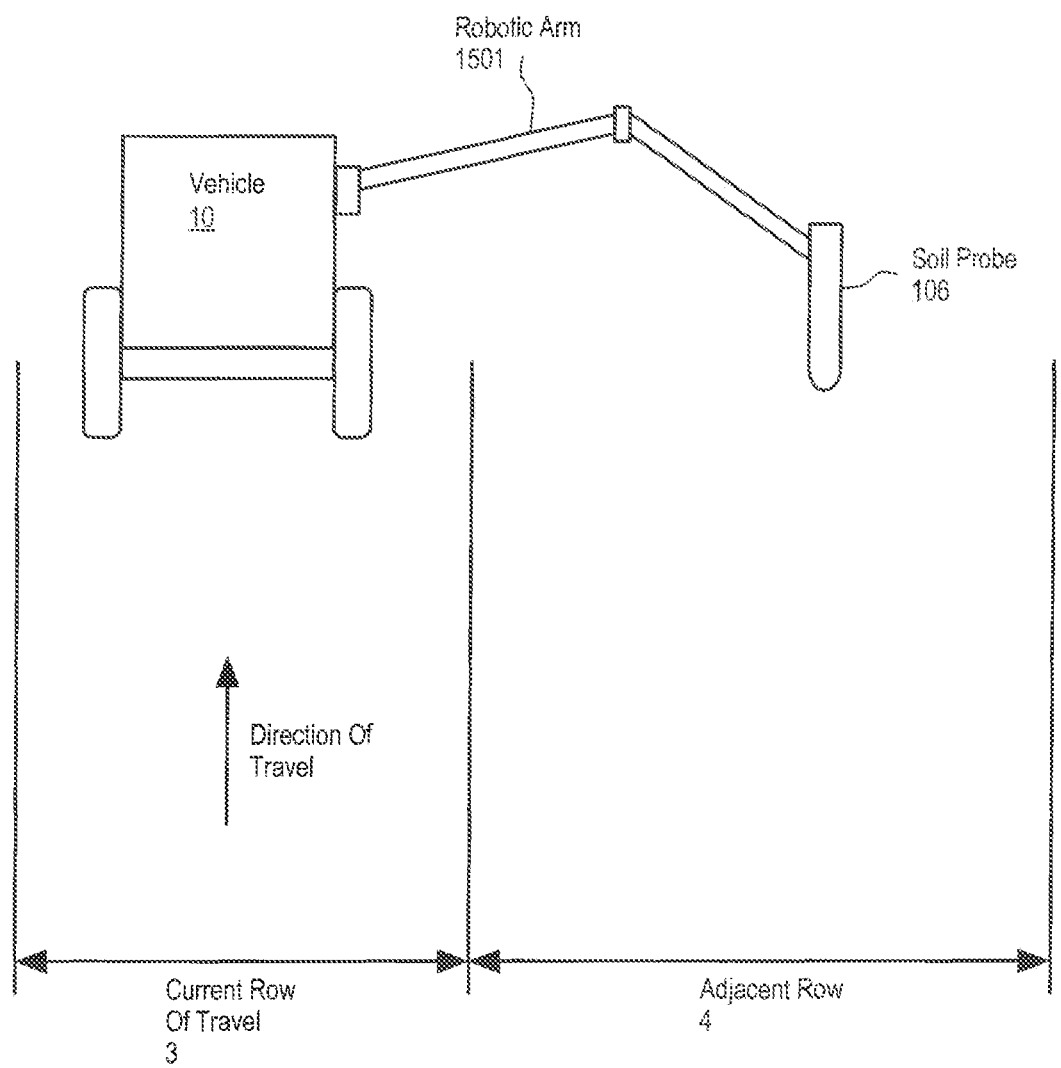
FIG. 25 illustrates a rear elevation view of a vehicle with soil probe according to one embodiment.

FIG. 25 illustrates a rear elevation view of a vehicle with soil probe according to one embodiment.

As illustrated in FIG. 25, collection system 15 can be configured to sample in a row adjacent to the current rows of travel. This provides time to process and test the sample to obtain a result that can be used to change an agricultural function on the vehicle 10 as vehicle 10 crosses the point. As shown in FIG. 25, any of the soil probes (e.g., 106) described above can be mounted to robotic arm 1501. Robotic arm 1501 is mounted to vehicle 10 and extends to an adjacent row 4. Robotic arm 1501 is in communication with CPU 2820. CPU 2820 sends a signal to robotic arm 1501 to extend to adjacent row 4 and to lower soil probe 106 into soil. Robotic arm 1501 then receives a signal from CPU 2820 to move robotic arm 1501 to vehicle 10 to have the soil collected in collection container 121 as described above.

To reduce the time it takes to process and then test soil and/or vegetation samples, provided are multiple testing systems each working in parallel to test samples while still collecting additional samples. Optionally, there can be multiple processing systems. The number of processing systems and testing systems can be chosen to account for the maximum speed of vehicle 10 during sampling and the number of samples to be taken per area. Depending on timing, one processing system can process all samples for testing in a testing system. Described herein is a system with multiple processing systems 2801. CPU 2820 can send a signal to a collection system to actuate and collect a sample and then deliver the sample to a first processing system 2801. CPU 2820 can then send a signal to processing system 2801 to process the sample. In the meantime, CPU 2820 can send a signal to the collection system to collect another sample and then deliver the sample to a second processing system. As each processing system completes processing, which can be based on a fixed amount of time, the sample can be transferred to via a transfer system (such as shown in FIGS. 11A to 12B) to an available testing system. A signal is sent from CPU 2820 to the transfer system to retrieve the sample. Once retrieved, CPU 2820 signals the transfer system to transfer the sample to an available testing system.

5. Implementation Example—Hardware Overview

FIG. 28 shows an example of a system 2800 that includes a machine 2802 (e.g., vehicle, tractor, combine harvester, etc.) and an implement 2840 (e.g., planter, cultivator, plough, sprayer, spreader, irrigation implement, etc.) in accordance with one embodiment. The machine 2802 includes a processing system 2820, memory 2805, machine network 2810 (e.g., a controller area network (CAN) serial bus protocol network, an ISOBUS network, etc.), and a network interface 2815 for communicating with other systems or devices including the implement 2840. The machine network 2810 includes sensors 2812 (e.g., sensors for measuring properties of soil and vegetative samples, speed sensors, etc.), controllers 2811 (e.g., GPS receiver, radar unit) for controlling and monitoring operations of the machine or implement. The network interface 2815 can include at least one of a GPS transceiver, a WLAN transceiver (e.g., WiFi), an infrared transceiver, a Bluetooth transceiver, Ethernet, or other interfaces from communications with other devices and systems including the implement 2840. The network interface 2815 may be integrated with the machine network 2810 or separate from the machine network 2810 as illustrated in FIG. 28. The I/O ports 2829 (e.g., diagnostic/on board diagnostic (OBD) port) enable communication with another data processing system or device (e.g., display devices, sensors, etc.).

In one example, the machine performs operations of a tractor or vehicle that is coupled to an implement for agricultural operations. The processing system 2820 may include one or more microprocessors, processors, a system on a chip (integrated circuit), or one or more microcontrollers. The processing system includes processing logic 2826 for executing software instructions of one or more programs and a communication unit 2828 (e.g., transmitter, transceiver) for transmitting and receiving communications from the machine via machine network 2810 or network interface 2815 or implement via implement network 2850 or network interface 2860. The communication unit 2828 may be integrated with the processing system or separate from the processing system. In one embodiment, the communication unit 2828 is in data communication with the machine network 2810 and implement network 2850 via a diagnostic/OBD port of the I/O ports 2829.

Processing logic 2826 including one or more processors may process the communications received from the communication unit 2828 including agricultural data (e.g., test data, testing results, GPS data, liquid application data, flow rates, etc.). The system 2800 includes memory 2805 for storing data and programs for execution (software 2806) by the processing system. The memory 2805 can store, for example, software components such as testing software for analysis of soil and vegetation samples for performing operations of the present disclosure, or any other software application or module, images (e.g., captured images of crops), alerts, maps, etc. The memory 2805 can be any known form of a machine readable non-transitory storage medium, such as semiconductor memory (e.g., flash; SRAM; DRAM; etc.) or non-volatile memory, such as hard disks or solid-state drive. The system can also include an audio input/output subsystem (not shown) which may include a microphone and a speaker for, for example, receiving and sending voice commands or for user authentication or authorization (e.g., biometrics).

In the embodiments with sampling system 2801 (e.g., processing system 2801), vehicle 2802 (e.g., machine 2802) can further include a sensing system 2812 or be coupled to an implement 2840 that includes a sensing system 2852. Sensing system (e.g., sensing system 2812, sensing system 2852) is in data communication with processing system 2820 (e.g., microprocessor(s), CPU). Additional data at each point sampled can be tested by the sensing system. Sensing system can include one or more of the following: spectrographic measurement, electrical conductivity, apparent electrical conductivity, LIDAR, radar, ground penetrating radar, sonar, optical height, camera, time of flight camera. Examples of spectrographic measurement include, but are not limited to, visible light, laser, near-infrared, infrared, transient infrared spectroscopy, RAMAN spectroscopy, ultraviolet, and x-ray. The combination of soil and/or vegetation sampling along with sensing can provide a more detailed analysis of the conditions in the field.

The processing system 2820 communicates bi-directionally with memory 2805, machine network 2810, network interface 2815, display device 2830, display device 2825, and I/O ports 2829 via communication links 2830-2836, respectively.

Display devices 2825 and 2830 can provide visual user interfaces for a user or operator. The display devices may include display controllers. In one embodiment, the display device 2825 is a portable tablet device or computing device with a touchscreen that displays data (e.g., test results of soil, test results of vegetation, liquid application data, captured images, localized view map layer, high definition field maps of as-applied liquid application data, as-planted or as-harvested data or other agricultural variables or parameters, yield maps, alerts, etc.) and data generated by an agricultural data analysis software application and receives input from the user or operator for an exploded view of a region of a field, monitoring and controlling field operations. The operations may include configuration of the machine or implement, reporting of data, control of the machine or implement including sensors and controllers, and storage of the data generated. The display device 2830 may be a display (e.g., display provided by an original equipment manufacturer (OEM)) that displays images and data for a localized view map layer, as-applied liquid application data, as-planted or as-harvested data, yield data, controlling a machine (e.g., planter, tractor, combine, sprayer, etc.), steering the machine, and monitoring the machine or an implement (e.g., planter, combine, sprayer, etc.) that is connected to the machine with sensors and controllers located on the machine or implement.

A cab control module 2870 may include an additional control module for enabling or disabling certain components or devices of the machine or implement. For example, if the user or operator is not able to control the machine or implement using one or more of the display devices, then the cab control module may include switches to shut down or turn off components or devices of the machine or implement.

The implement 2840 (e.g., planter, cultivator, plough, sprayer, spreader, irrigation implement, etc.) includes an implement network 2850, a processing system 2862, a network interface 2860, and optional input/output ports 2866 for communicating with other systems or devices including the machine 2802. In one example, the implement network 2850 (e.g., a controller area network (CAN) serial bus protocol network, an ISOBUS network, etc.) includes a pump 2856 for pumping liquid from a storage tank(s) 2890 to control monitoring units (CMUs) 2880, 2881, . . . N of the implement, sensors or sensing system 2852 (e.g., soil sensors, vegetation sensors, soil probe, speed sensors, seed sensors for detecting passage of seed, downforce sensors, actuator valves, OEM sensors, flow sensors, etc.), controllers 2854 (e.g., GPS receiver), and the processing system 2862 for controlling and monitoring operations of the machine. The CMUs control and monitor the application of the liquid to crops or soil as applied by the implement. The liquid application can be applied at any stage of crop development including within a planting trench upon planting of seeds, adjacent to a planting trench in a separate trench, or in a region that is nearby to the planting region (e.g., between rows of corn or soybeans) having seeds or crop growth. Alternatively, solids can be applied via the spreader.

The OEM sensors may be moisture sensors or flow sensors for a combine, speed sensors for the machine, seed force sensors for a planter, liquid application sensors for a sprayer, or vacuum, lift, lower sensors for an implement. For example, the controllers may include processors in communication with a plurality of seed sensors. The processors are configured to process data (e.g., testing data for soil and vegetation, liquid application data, seed sensor data) and transmit processed data to the processing system 2862 or 2820. The controllers and sensors may be used for monitoring motors and drives on a planter including a variable rate drive system for changing plant populations. The controllers and sensors may also provide swath control to shut off individual rows or sections of the planter. The sensors and controllers may sense changes in an electric motor that controls each row of a planter individually. These sensors and controllers may sense seed delivery speeds in a seed tube for each row of a planter.

The network interface 2860 can be a GPS transceiver, a WLAN transceiver (e.g., WiFi), an infrared transceiver, a Bluetooth transceiver, Ethernet, or other interfaces from communications with other devices and systems including the machine 2802. The network interface 2860 may be integrated with the implement network 2850 or separate from the implement network 2850 as illustrated in FIG. 28.

The processing system 281262 communicates bi-directionally with the implement network 2850, network interface 2860, and I/O ports 2866 via communication links 2841-2843, respectively.

The implement communicates with the machine via wired and possibly also wireless bi-directional communications 2804. The implement network 2850 may communicate directly with the machine network 2810 or via the networks interfaces 2815 and 2860. The implement may also by physically coupled to the machine for agricultural operations (e.g., planting, harvesting, spraying, etc.).

The memory 2805 may be a machine-accessible non-transitory medium on which is stored one or more sets of instructions (e.g., software 2806) embodying any one or more of the methodologies or functions described herein. The software 2806 may also reside, completely or at least partially, within the memory 2805 and/or within the processing system 2820 during execution thereof by the system 2800, the memory and the processing system also constituting machine-accessible storage media. The software 2806 may further be transmitted or received over a network via the network interface 2815.

In one embodiment, a machine-accessible non-transitory medium (e.g., memory 2805) contains executable computer program instructions which when executed by a data processing system cause the system to perform operations or methods of the present disclosure including measuring properties and testing of soil and vegetative samples. While the machine-accessible non-transitory medium (e.g., memory 1205) is shown in an exemplary embodiment to be a single medium, the term "machine-accessible non-transitory medium" should be taken to include a single medium or multiple media (e.g., a centralized or distributed database, and/or associated caches and servers) that store the one or more sets of instructions. The term "machine-accessible non-transitory medium" shall also be taken to include any medium that is capable of storing, encoding or carrying a set of instructions for execution by the machine and that cause the machine to perform any one or more of the methodologies of the present disclosure. The term "machine-accessible non-transitory medium" shall accordingly be taken to include, but not be limited to, solid-state memories, optical and magnetic media, and carrier wave signals.

Data from soil and/or vegetation sampling can be used to generate a map of the field to be used later during an agricultural operation, such as nutrient application.

What is claimed is:

1. An agricultural implement for acquiring a soil sample comprising:
a vehicle;
a sampling implement supported by the vehicle on a front axle housing and underneath a body of the vehicle, the sampling implement configured to acquire a soil sample, wherein the sampling implement comprises a side collection port configured to receive the soil sample and a device configured to eject the sample from the side collection port into a collection container, wherein the device includes a rod disposed adjacent to the side collection port and a scooper disk attached to the rod and aligned with the side collection port, and wherein rotation of the rod causes the scooper disk to scoop the sample out of the side collection port, thereby ejecting the sample;
a soil processing system for preparing the sample, wherein the collection container is configured to move between the sampling implement and the soil processing system; and
a test strip apparatus configured to hold one or more test strips and guide the one or more test strips through the sample.

2. The agricultural implement of claim 1, wherein the test strip apparatus comprises an ion-selective electrode immersed in the sample and configured to communicate a test result for the sample to the soil processing system.

3. The agricultural implement of claim 1, wherein the test strip apparatus comprises a spectrophotometer configured to analyze the sample.

4. The agricultural implement of claim 1, wherein the test strip apparatus further comprises:
a reel; and
a pouch strip wound onto the reel.

5. The agricultural implement of claim 4, wherein
the pouch strip comprises a plurality of pouches,
each pouch of the plurality of pouches storing a reagent.

6. The agricultural implement of claim 5, wherein the test strip apparatus further comprises a test syringe being driven to dip into each pouch.

7. The agricultural implement of claim 4, wherein the test strip apparatus further comprises one or more drive strips on each side of the pouch strip.

8. The agricultural implement of claim 7, wherein the test strip apparatus further comprises at least one strip drive wheel powered to drive the one or more drive strips.

9. The agricultural implement of claim 7, wherein the test strip apparatus further comprises:
a sprocket drive wheel; and
wherein a drive strip of the one or more drive strips comprises one or more sprocket holes and is driven by the sprocket drive wheel.

10. The agricultural implement of claim 1, wherein the test strip apparatus comprises:
a dispensing wheel;
a collecting wheel;
at least one roller between the dispensing wheel and collecting wheel;
a test strip holder wound from the dispensing wheel around the roller to the collecting wheel;
a motor for driving the collecting wheel;
a colorimeter; and
a plurality of test strips disposed on the test strip holder for contacting a solution containing the sample,
the colorimeter configured to test a specific test strip of the plurality of test strips after the specific test strip contacts the solution containing the sample and indicates a color corresponding to a concentration of a chemical in the solution.

11. The agricultural implement of claim 10, wherein at least one of the plurality of test strips comprises an identification disposed on the test strip holder indicating a location where the sample was taken.

12. The agricultural implement of claim 10, wherein the test strip apparatus further comprises one or more guide rollers being driven to guide a test strip of the plurality of test strips.

13. The agricultural implement of claim 10, wherein the test strip holder is configured to hold multiple test strips side by side, wherein each test strip of the multiple test strips is reactive to a different chemical.

14. The agricultural implement of claim 10, wherein the at least one processing system is configured to generate a data map that shows test results generated by the colorimeter for each chemical tested at each location.

15. The agricultural implement of claim 10, wherein the test strip apparatus is configured to submerge the specific test strip into the solution.

16. The agricultural implement of claim 10, wherein:
the test strip apparatus further comprises a sample container holding the solution, and
the sample container is configured to rise, submerging the specific test strip into the solution.

* * * * *